United States Patent
Weiss

(10) Patent No.: US 10,472,406 B2
(45) Date of Patent: *Nov. 12, 2019

(54) INSULIN ANALOGUES WITH SELECTIVE SIGNALING PROPERTIES AND REDUCED MITOGENICITY

(71) Applicant: CASE WESTERN RESERVE UNIVERSITY, Cleveland, OH (US)

(72) Inventor: Michael Weiss, Moreland Hills, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/545,189

(22) PCT Filed: Jan. 20, 2016

(86) PCT No.: PCT/US2016/014136
§ 371 (c)(1),
(2) Date: Jul. 20, 2017

(87) PCT Pub. No.: WO2016/118631
PCT Pub. Date: Jul. 28, 2016

(65) Prior Publication Data
US 2017/0369548 A1    Dec. 28, 2017

Related U.S. Application Data

(60) Provisional application No. 62/105,713, filed on Jan. 20, 2015.

(51) Int. Cl.
C07K 14/62 (2006.01)
A61P 3/10 (2006.01)
A61K 38/00 (2006.01)

(52) U.S. Cl.
CPC .............. *C07K 14/62* (2013.01); *A61K 38/00* (2013.01)

(58) Field of Classification Search
None
See application file for complete search history.

(56) References Cited

U.S. PATENT DOCUMENTS

2011/0166064 A1*  7/2011  Weiss .................... C07K 14/62
                                                        514/6.3
2014/0128319 A1    5/2014  Weiss

FOREIGN PATENT DOCUMENTS

AU    2013237740       10/2013
WO    2010014946        2/2010
WO    WO-2013158618 A1 * 10/2013  ............ A61K 38/28

* cited by examiner

*Primary Examiner* — Julie Ha
*Assistant Examiner* — Kristina M Hellman
(74) *Attorney, Agent, or Firm* — Hahn Loeser & Parks, LLP; John J. Cunniff

(57) ABSTRACT

A two-chain insulin analog contains Aspartic Acid at position B10 and penta-fluoro-Phenylalanine at position B24, optionally Histidine or Glutamic Acid at position A8, optionally additional substitutions or modifications at positions A13 and/or A14 and/or B28 and/or B29. The analog may be an analog of a mammalian insulin, such as human insulin, may optionally include (i) N-terminal deletion of one, two or three residues from the B chain, (ii) a mono-peptide or dipeptide C-terminal extension of the B-chain containing at least one acidic residue, and (iii) other modifications known in the art to enhance the stability of insulin. Formulations of the above analogs at successive strengths U-100 to U-1000 in soluble solutions at least pH value in the range 7.0-8.0 in the absence or presence of zinc ions at a molar ratio of 0.00-0.10 zinc ions per insulin analog monomer.

12 Claims, 12 Drawing Sheets
Specification includes a Sequence Listing.

PROINSULIN

MODEL

INSULIN ANALOGUES WITH SELECTIVE SIGNALING PROPERTIES AND REDUCED MITOGENICITY

STATEMENT REGARDING FEDERALLY SPONSORED RESEARCH OR DEVELOPMENT

This invention was made with government support awarded by the National Institutes of Health under grant numbers DK040949 and DK074176. The U.S. government has certain rights to the invention.

BACKGROUND OF THE INVENTION

This invention relates to polypeptide hormone analogues that exhibit enhanced pharmaceutical properties, such as increased thermodynamic stability, decreased mitogenicity, and feasibility of a rapid-acting formulation at high protein concentrations (1-5 mM) in the absence of zinc ions. More particularly, this invention relates to insulin analogues that confer altered or selective post-receptor signaling properties (relative to signaling by wild-type insulin). The insulin analogues of the present invention thus consist of two polypeptide chains that contain a novel combination of amino-acid substitutions such that the analogues exhibit (i) enhanced thermodynamic stability, (ii) decreased self-association at protein concentrations greater than 0.6 mM, and (iii) at least a portion of the biological potency of the human insulin molecule, although a greater number of protein molecules may be required, on subcutaneous or intravenous injection in a mammal, to elicit a similar reduction in blood-glucose concentration.

The engineering of non-standard proteins, including therapeutic agents and vaccines, may have broad medical and societal benefits. Naturally occurring proteinsas encoded in the genomes of human beings, other mammals, vertebrate organisms, invertebrate organisms, or eukaryotic cells in general—may have evolved to function optimally within a cellular context but may be suboptimal for therapeutic applications. Analogues of such proteins may exhibit improved biophysical, biochemical, or biological properties. A benefit of protein analogues would be to achieve enhanced "on-target" activity (such as metabolic regulation of metabolism leading to reduction in blood-glucose concentration) with decreased unintended and unfavorable side effects, such as promotion of the growth of cancer cells or increased biosynthesis of lipids. Another benefit of such protein engineering would be preservation of rapid onset of action on concentration of the protein to achieve formulations of higher strength. Yet another example of a societal benefit would be augmented resistance to degradation at or above room temperature, facilitating transport, distribution, and use. An example of a therapeutic protein is provided by insulin. Wild-type human insulin and insulin molecules encoded in the genomes of other mammals bind to insulin receptors is multiple organs and diverse types of cells, irrespective of the receptor isoform generated by alternative modes of RNA splicing or by alternative patterns of post-translational glycosylation. Wild-type insulin also binds with lower but significant affinity to the homologous Type 1 insulin-like growth factor receptor (IGF-1R).

Insulin is a two-chain protein molecule that in a vertebrate animal is the biosynthetic product of a single-chain precursor, designated proinsulin. The sequence and structure of human proinsulin are illustrated in FIGS. 1A and 1B, respectively; the sequence of human insulin is shown in FIG. 1C. The two polypeptide chains of insulin are respectively designated A and B. Specific residues in one or the other chain are designated below by standard three letter code (for example, Ala for Alanine or Asp for Aspartic Acid) followed by a superscript that designates the chain (A or B) and residue number in that chain. For example, Histidine at position 10 of the B chain is designated $His^{B10}$, Valine at position 12 of the B chain is designated $Val^{B12}$, and Threonine at position 8 of the A chain is designated $Thr^{A8}$. "Insulin analogues" designate a class of molecules related to wild-type insulin by substitution of one more amino-acid residues by a different type of amino acid or by modifications of one or more atoms in the side chain or main chain of such residues by a different atom or set of atoms. An example of an insulin analogue known in the art is insulin lispro, in which $Pro^{B28}$ is substituted by Lys and $Lys^{B29}$ is substituted by Pro. Insulin lispro (also designated KP-insulin) is the active component of the product Humalog® (Eli Lilly and Co.).

It is known in the art that the B chain of insulin may be modified through standard amino-acid substitutions at one or a few positions to enhance the rate of absorption of an insulin analogue formulation from the subcutaneous depot. An example of a further medical benefit would be optimization of the pharmacokinetic properties of a soluble insulin analogue formulation such that rapid onset of action is retained in formulations of strengths in the range U-200 through U-1000, i.e., between twofold and tenfold higher than conventional U-100 insulin products (in this nomenclature "U-X" designates X internal units per ml of solution or suspension). Insulin formulations of increased strength promise to be of particular benefit for patients who exhibit marked insulin resistance and may also be of value in internal or external insulin pumps, either to extend the reservoir life or to permit miniaturization of the reservoir in a new generation of pump technologies. Existing insulin products typically exhibit prolonged pharmacokinetic and pharmacodynamics properties on increasing the concentration of the insulin or insulin analogue to achieve formulation strengths>U-200 (200 international units/ml). Such prolongation impairs the efficacy of such products for the prandial control of glycemia on subcutaneous injection and impairs the efficacy and safety of pump-based continuous subcutaneous infusion. In light of these disadvantages, the therapeutic and societal benefits of rapid-acting insulin analogue formulations would be enhanced by the engineering of insulin analogues that retain rapid action at strengths between U-200 and U-1000. Additional benefits would accrue if the novel soluble insulin analogue exhibited weaker affinity for the Type 1 IGF receptor relative to wild-type human insulin. Still additional therapeutic and societal benefit would accrue if the concentrated insulin analogue formulation should exhibit reduced mitogenicity in assays developed to monitor insulin-stimulated proliferation of human cancer cell lines.

Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinopathy, blindness, and renal failure. Although the importance of glycemic control is well known in the art, the pathophysiology of type 2 diabetes mellitus (T2DM) is also characterized by selective insulin resistance (SIR) where insulin becomes ineffective at glycemic control and yet continues to drive mitogenicity and excess lipid synthesis. Accumulating lipid in the liver and muscle further unbalances glucose regulation, increases insulin resistance, and accelerates the progression of T2DM and its complications. To our knowledge, there are presently no insulin products (approved or in clinical trials) that rebalance such perturbed cellular and organ-specific signaling. We thus anticipate that such a product would create a new treatment paradigm in T2DM, yielding significant long-term health benefits and reduction in aggregate health-care costs.

Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain. A variety of evidence indicates that it consists of an insulin-like core and disordered connecting peptide. Formation of three specific disulfide bridges (A6-A11, A7-B7, and A20-B19) is coupled to oxidative folding of proinsulin in the rough endoplasmic reticulum (ER). Proinsulin is coverted to insulin in the trans-Golgi network en route to storage as zinc insulin hexamers in the glucose-regulated secretory granules within pancreatic beta-cells. The classical crystal structure of insulin (one protomer extracted from the zinc hexamer) is shown in FIG. 2.

The present invention was motivated by medical and societal needs to engineer a rapid-acting insulin analogue in a soluble formulation at neutral pH at strengths in the range U-100 through U-1000 that exhibits altered or selective post-receptor signaling properties. A barrier to such products has long been posed by the prevailing paradigm of how binding to the insulin receptor leads to transmission of a signal across the cellular membrane, leading to autophosphorylation of the cytoplasmic portion of the receptor. Such autophosphorylation in turn activates a variety of post-receptor signaling pathways, such as pathways leading to (i) translocation of the GLUT4 glucose transporter from an intracellular compartment to the plasma membrane, (ii) transcriptional activation of genes promoting the growth and proliferation of cancer cells, (iii) storage of glucose molecules within the cell as glycogen, and (iv) metabolic transformation of the insulin molecule through the intracellular biosynthesis of lipids.

It is not known in general whether or how the insulin molecule may be modified such that one post-receptor signaling pathway may be selectively strengthened or attenuated. The structure of the intact insulin receptor has not to date been determined, and so the mechanism of how binding of insulin to the outside of the cell (the "ectodomain" of the receptor) of the receptor) leads to propagation of a signal to the inside of the cell (i.e., to the cytoplasmic domain of the receptor) is not known. A crystal structure of the apo-ectodomain is known in the art as an inverted-V dimeric assembly at low resolution (FIG. 3) but crystals could not obtained with an insulin molecule bound. The crystal structure of insulin bound to a domain-minimized "micro-receptor" has also been determined at low resolution (FIG. 4), but this construction lacks the beta-subunit of the receptor required for trans-membrane signaling and communication of a signal to post-receptor pathways. Accordingly, it is not known in the art whether or how modification of the insulin molecule might affect the relative strength of various post-receptor signaling outputs.

An insulin analogue known in the art to exhibit an unfavorable change in the balance of post-receptor signaling is provided by $Asp^{B10}$-insulin. The original motivation for the design and preparation of this analogue was based on its structural role in insulin self-assembly. The wild-type residue ($His^{B10}$) functions in native hexamer assembly to coordinate the two axial zinc ions in the central axis of the hexamer. Substitution of $His^{B10}$ by Asp impairs the binding of zinc ions in this axial mode and blocks higher-order self-assembly via the trimer-related surface of the classical hexamer. $Asp^{B10}$ may be expected on general grounds by enhance the segmental stability of the central B-chain α-helix in the zinc-free monomer or dimer via electrostatic mechanisms: as a favorable C-Cap residue and through potential formation of an (i, i+4) salt bridge. Irrespective of the theoretical underpinnings of protein stability, substitution of $His^{B10}$ by Asp was observed indeed to augment the thermodynamic stability of the zinc-free insulin monomer as probed by chemical-denaturation studies. $Asp^{B10}$ also enhances the affinity of insulin for the insulin receptor and augments in parallel its potency to stimulate lipogenesis in isolated adipocytes.

Despite the above favorable structural and biophysical properties conferred by substitution of $His^{B10}$ by Asp in wild-type insulin, its clinical use was precluded by increased mitogenicity in cell-culture assays of neoplastic cell lines (including a cell line derived from a human breast cancer) in association with the finding of an excess incidence of mammary tumors on chronic treatment of Sprague-Dawley rats by $Asp^{B10}$-insulin relative to wild-type insulin. The present invention provides a combination of a non-standard amino-acid substitution in the insulin molecule (penta-fluoro-$Phe^{B24}$) such that the favorable properties conferred by $Asp^{B10}$ (such as enhanced stability and impaired self-assembly beyond the stage of dimerization) are retained whereas the unfavorable increase in mitogenicity in cell-culture assay is mitigated or even reserved to achieve a level of mitogenicity lower than that of wild-type insulin itself. As a further surprise, the combination of $Asp^{B10}$ with penta-fluoro-$Phe^{B12}$ favorable alters the balance of post-receptor signaling pathways in muscle such that formation of glycogen is enhanced relative to formation of lipids.

SUMMARY OF THE INVENTION

A surprising aspect of the present invention is that these complementary goals can be achieved by co-introduction of the acidic $Asp^{B10}$ substitution with an amino-acid substitution in the C-terminal β-strand of the B chain ($Phe^{B24}$→penta-fluoro-Phe), a modification that by itself markedly impairs the biological activity of insulin. This pair of modifications may further be combined with (i) an amino-acid substitution in the C-terminal segment of the B chain ($Lys^{B29}$→Glu) previously paired with a basic substitution in the N-terminal segment of the B chain ($Asn^{B3}$→Lys) for an unrelated purpose, to whit., design of a prandial insulin analogue competent for self-assembly; or (ii) other substitutions at positions B28 and/or B29 intended to decrease the strength of dimerization or to remove the tryptic site ordinarily associated with the presence of Lys at position B29 in wild-type insulin. The insulin analogues of the present invention thus contain as a core design element the above B10 and B24 modifications based on our surprising observation that this combination retains or enhances the advantageous biophysical properties of Asp$^{B10}$ while conferring novel signaling properties and mitigating or avoiding its disadvantageous properties. Insulin analogues of the present invention may also contain non-β-branched substitutions at position A8, C-terminal extensions of the B chain to include residue B31 (a 31-residue B-chain or residues B31-B32 (a 32-residue B chain). The above set of analogues may optionally further be modified by deletion of N-terminal B-chain residues B1, B1-B2, or B1-B3.

It is a second surprising aspect of the present invention is that insulin analogues can at the same time be designed to exhibit impaired self-assembly—and therefore rapid action on subcutaneous assembly—and yet maintain sufficient stability with respect to chemical and physical degradation as to permit their safe and effective formulation as a practical insulin product. Such stability is also a consequence of the combined properties conferred by Asp$^{B10}$ and penta-fluoro-Phe$^{B24}$. It comes as a further surprise that the above may be accompanied by reduction in mitogenicity. We envisage that the products of the present invention will disproportionately benefits patients in Western societies with obesity, Type 2 diabetes mellitus and marked insulin resistance. Such clinical features pose a growing burden to under-represented minorities, including African-Americans, Hispanic-Americans and indigenous American tribes. Due to their enhanced biological activity per nanomole of protein, products of the present invention will also be useful in extending the reservoir life of insulin pumps and in enabling the miniaturization of such pumps.

It is, furthermore, an aspect of the present invention to provide insulin analogues that provide rapid-acting pharmacokinetic and pharmacodynamics properties on subcutaneous injection. The analogues of the present investion contain Aspartic Acid at position B10 (Asp$^{B10}$), penta-fluoro-Phe at position B24 (5F-Phe$^{B24}$), and in one embodiment, also Glutamic Acid or Ornithine at B29 (Glu$^{B29}$ or Orn$^{B29}$); optionally, such analogues may contain a non-β-branched amino-acid substitution at position A8, a C-terminal extension of the B chain up to and including two residues (B31 and B32), and/or an N-terminal deletion of the B chain up to and including three residues (B1-B3). Residue B28 may be Pro (as in wild-type insulin), Lys, Gln, or Ala. Position A13 may optionally be Leu, Trp or Tyr; position A14 may optionally be Tyr or Glu. Residue B30 may optionally be absent. The insulin analogues of the present invention may also optionally contain standard or non-standard amino-acid substitutions at other sites in the A or B domains, such as positions B28 known in the art to confer rapid action, and may optionally contain one- or two-residue extensions of the B chain (residues B31 and B32). It is an additional aspect of the present invention that the analogues exhibit thermodynamic stabilities equal to or greater than that of wild-type human insulin, and mitogenicities in a tissue-culture assay of a human breast-cancer cell line equal to or less than that of wild-type human insulin.

The above combination of features is conferred by a novel combination of an acidic amino-acid substitution at position B10 and penta-fluoro-Phenylalanine at position B24. Although not wishing to be constrained by theory, we imagine that the inverted quadrapolar electrostatic moment of the aromatic ring of penta-fluor-Phe$^{B24}$, when docked at the hormone-receptor interface (FIG. 4), mitigates the effect of Asp$^{B10}$ to prolong the residence time and enhance the affinity of the three homologous hormone-receptor complexes (IR-A, IR-B and IGF-1R). We further imagine that in the free hormone the substitution of Phe$^{B24}$ by penta-fluoro-Phe preserves and augments the stabilizing effects of Asp$^{B10}$ as known in the art. Although not wishing to be constrained by theory, we envision that any structural perturbation to the native Leu$^{B15}$-phe$^{B24}$ interaction caused by the penta-fluoro-Phe$^{B24}$ substitution is balanced by the greater hydrophobicity of the modified aromatic ring within a crevice in the insulin molecule (FIG. 5). Also without wishing to be constrained by theory, we further imagine that non-additive effects of optional acid substitutions at positions A8, A14, and/or B29 attenuates mitogenic signaling by the complex of such analogues and the insulin receptor or by complexes of such analogues with the Type 1 IGF receptor.

In general, the present invention provides an insulin analogue containing Aspartic Acid at position B10, penta-fluoro-Phenylalanine at position B24, and optionally other amino-acid substitutions at one or more of the following three positions: A8, A13, A14, B28, B29, and optionally C-terminal extension of the B chain (to include B31 or B31-B32 where at least one of the additional residues is acidic), or N-terminal deletion of the B chain (up to and including B3). The present invention thus pertains to a novel class of insulin analogues containing a combination of modifications that together provide the long-sought clinical advantages not conferred by any one of the constituent modications. In one version of an analogue of the present invention, residues B28 and B29 are Lys$^{B28}$ and Pro$^{B29}$ as in a rapid-acting insulin analogue known in the art (insulin lispro; also designated KP-insulin). In other versions residue B28 is Proline (as in wild-type insulin) whereas residue B29 is Ornithine (Orn) or Glutamic Acid. In yet another version of the present invention residue B30 is absent. In yet another version the analogues of the present invention may contain Glutamic Acid at position A14, and/or Glycine, Alanine or Aspartic Acid at position A21.

DETAILED DESCRIPTION OF THE INVENTION

Figure 1A:
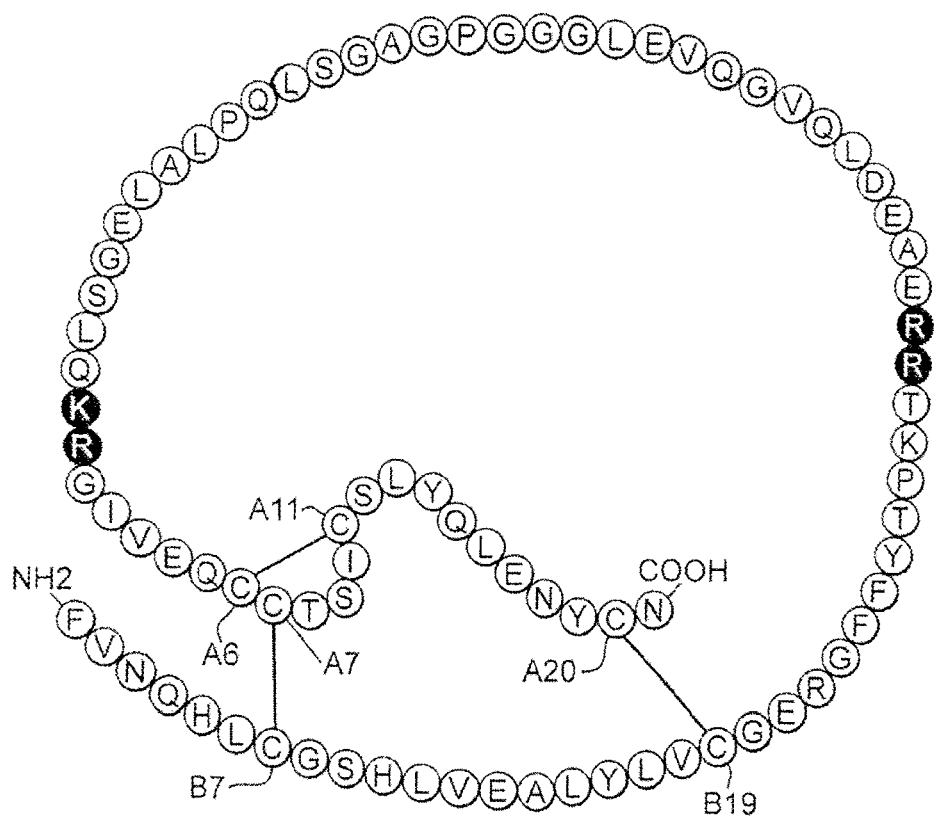
FIG. 1A is a schematic representation of the sequence of human proinsulin including the A- and B-chains and the connecting region shown with flanking dibasic cleavage sites (filled circles) and C-peptide (open circles).
Figure 1B:
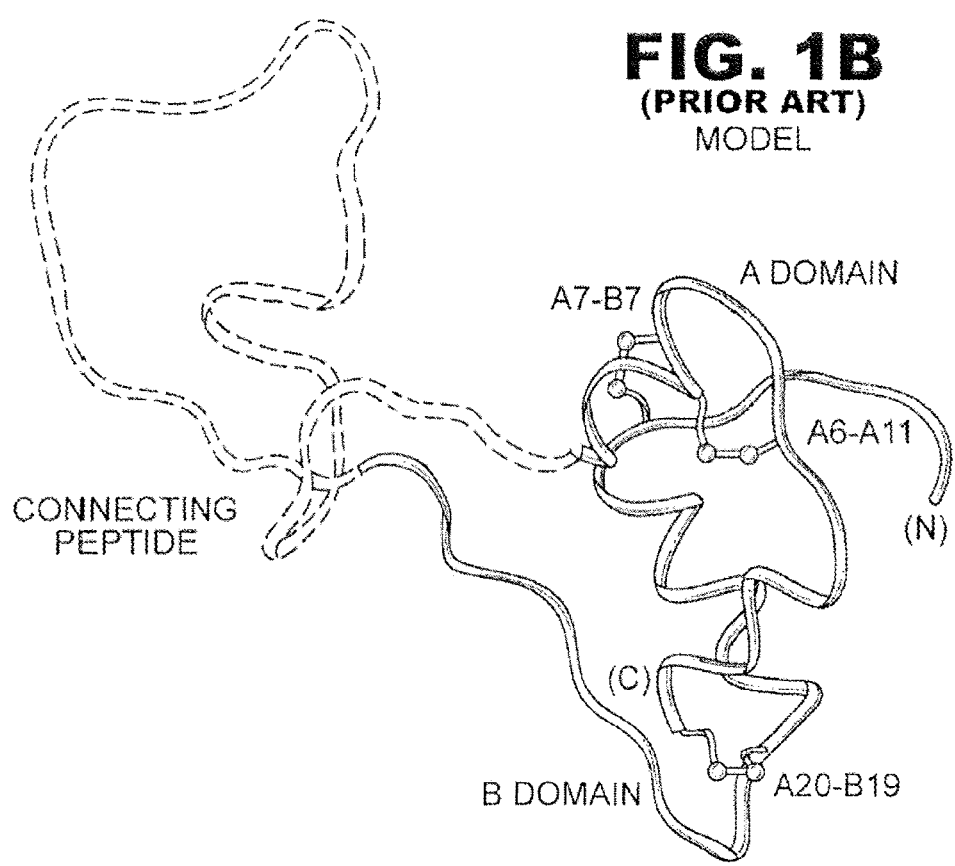
FIG. 1B is a structural model of proinsulin, consisting of an insulin-like moiety and a disordered connecting peptide (dashed line).
Figure 1C:
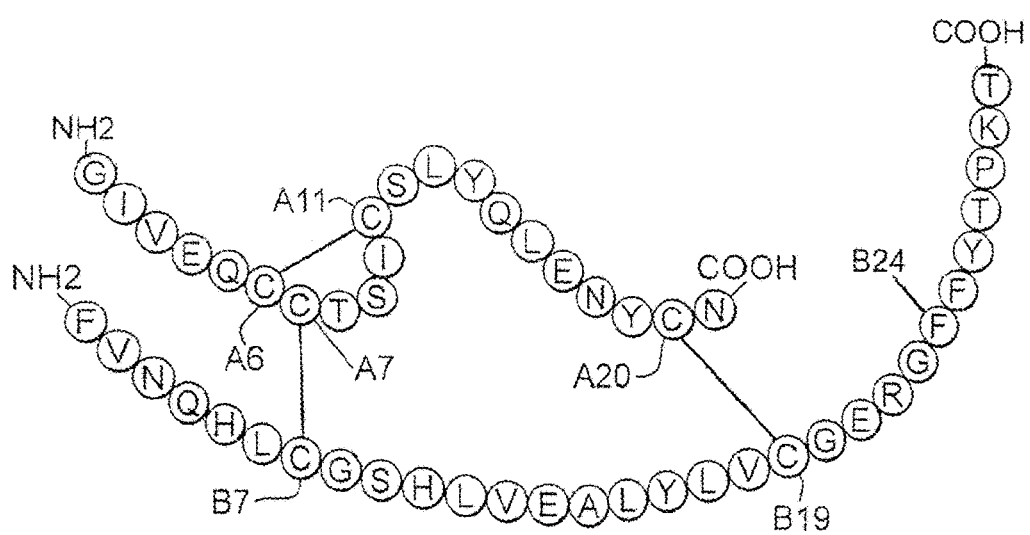
FIG. 1C is a schematic representation of the sequence of human insulin indicating the position of residues B27 and B30 in the B-chain.
Figure 2:
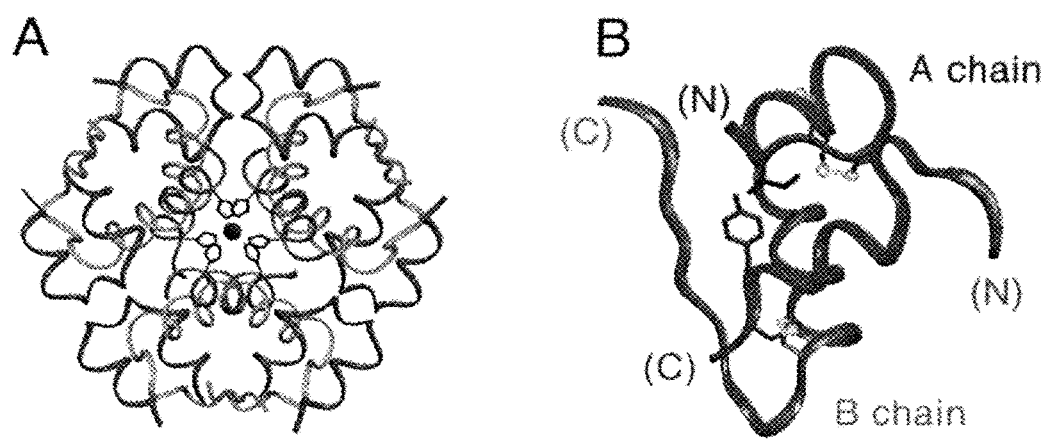
FIG. 2 depicts the structure of insulin. (A) The phenol-stabilized R$_6$ zinc hexamer. Axial zinc ions (overlaid) are shown as coincident black spheres coordinated by histidine side chains. (B) Structure of an insulin monomer. The disulfide brides are depicted as balls and sticks.
Figure 3:
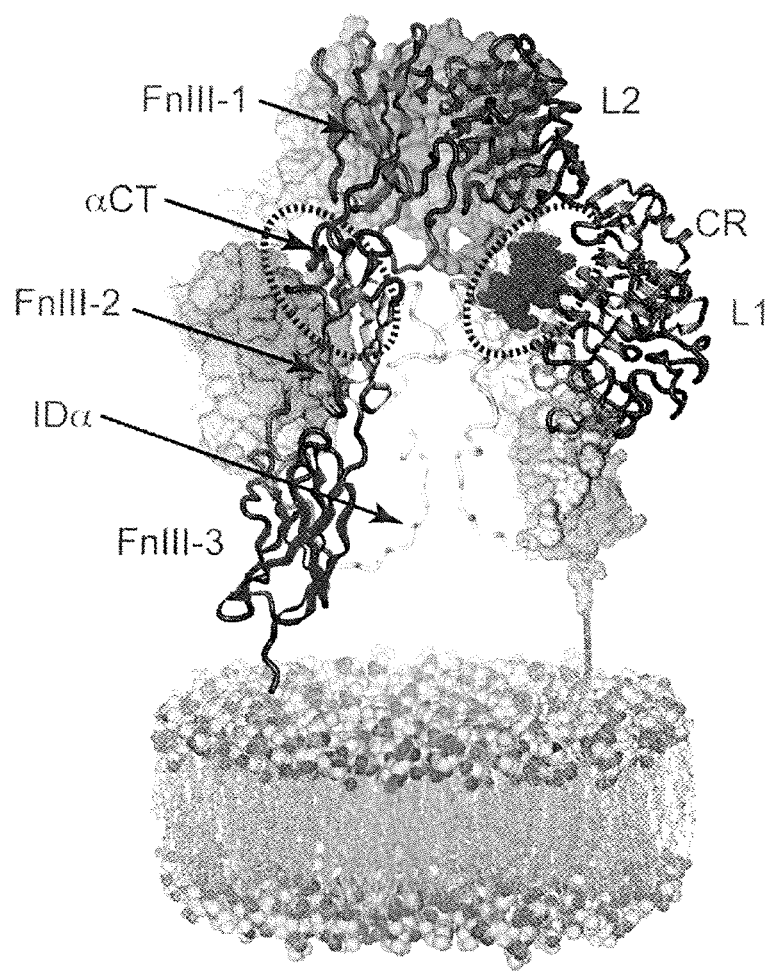
FIG. 3 illustrates the structure of the insulin-receptor (IR) ectodomain dimer. One subunit is shown in a ribbon representation, and the other as a space-filling surface. The position of the cell membrane is shown in schematic fashion at bottom. Coordinates were obtained from Protein Databank entry 3LOH.
Figure 4:
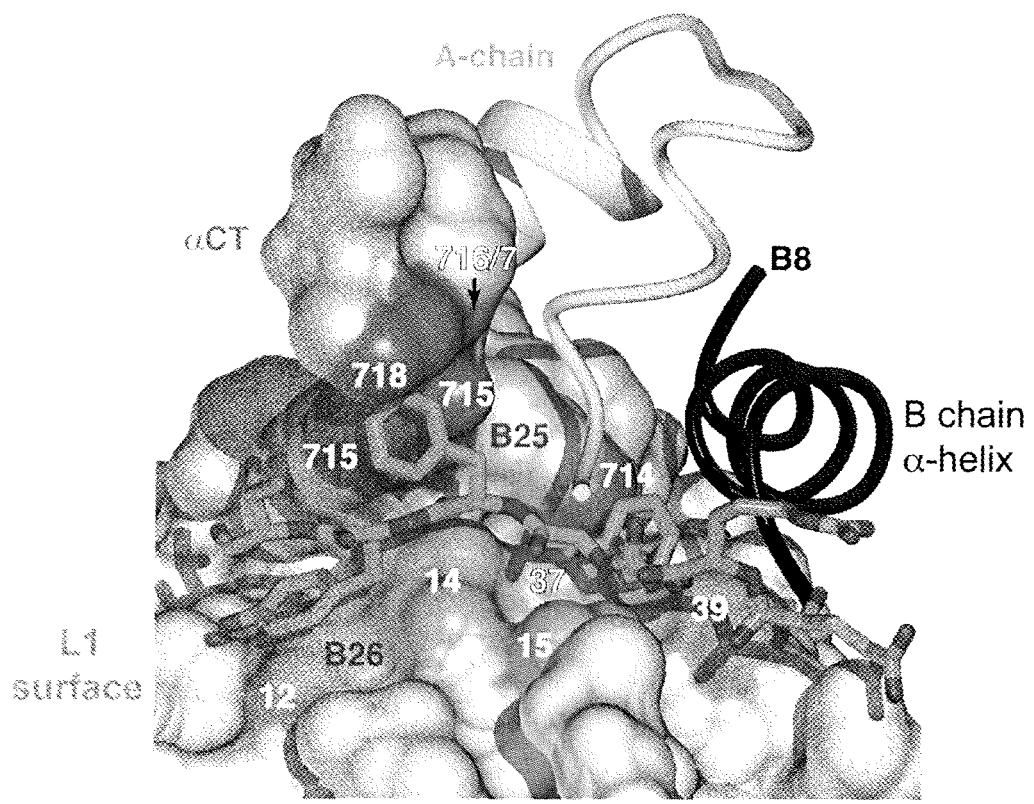
FIG. 4 illustrates how insulin binds to the ectodomain of its receptor. The "micro-receptor" structure represents a ternary complex containing insulin, an aCT peptide, and ectodomain a-subunit fragment L1-CR (Protein Databank entry 3W11). Polypeptide chains and domains are as labeled. Disulfide bridges are not shown.
Figure 5:
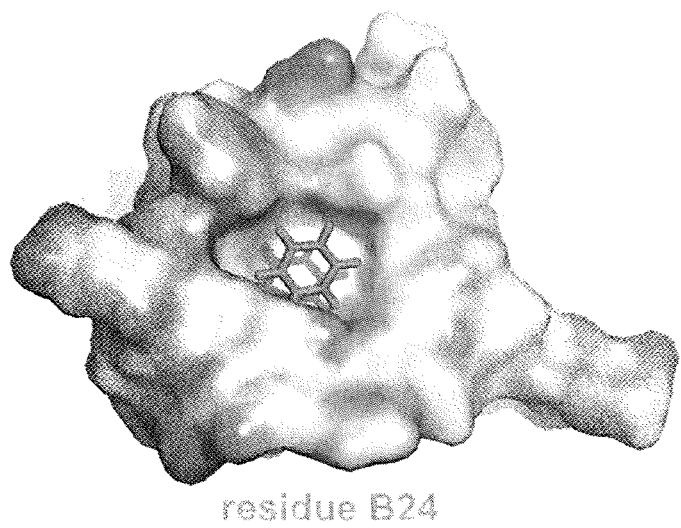
FIG. 5 depicts how Phe$^{B24}$ packs in a protein crevice. The aromatic side chain of Phe$^{B24}$ (sticks) sites within a crevice in the hydrophobic core whose borders and lip exhibit partial positive- and negative electrostatic protein surfaces.

The present invention is directed toward an insulin analogue that provides altered or selective post-receptor insulin signaling properties, rapid action under a broad range of protein concentrations and formulation strengths (typically from U-100 to U-500 and optionally as high as U-1000), affinity for the IGF-1R less than that of wild-type human insulin, and thermodynamic stability in the absence of zinc ions that is greater than that of wild-type human insulin relative to the baseline stability of wild-type human insulin in the absence of zinc ions.

It is an aspect of the present invention that the present analogues exhibit mitogenicities in a cell-based assay of human breast-cancer cellular proliferation in soft agar that are less than or equal to the mitogenicity of wild-type human insulin. It is yet another aspect of the present invention that the present analogues preferentially direct the flow of glucose-derived carbon atoms within muscle cells into glycogen relative to the flow of such carbon atoms into lipid. These aspects provide examples of "bias" in post-receptor signaling whereby favorable signaling outcomes are maintained or enhanced but unfavorable signaling outcomes are attenuated.

It is an aspect of the present invention that rapid absorption kinetics from a subcutaneous depot may be generated by an insulin analogue that is monomeric or dimeric—but not is a higher-order state of self-assembly—in a zinc-free solution at neutral pH at a protein concentration of 0.6-6.0 mM (as calculated in relation to the formal monomer concentration). Conventional prandial products, as known in the art, represent a continuum of possible coupled equilibria between states of self-assembly, including zinc-stabilized or zinc-ion-independent hexamers extended by potential hexamer-hexamer interactions. Molecular implementation of this strategy provides a novel class of insulin analogues that (i) are as stable or more stable as a zinc-free monomer and dimer relative to wild-type human insulin and (ii) retain at least a portion of the biological potency of wild-type human insulin (as assessed by hormone-regulated reduction in blood-glucose concentration) on a per-molecular or per-nanomole basis. It is an aspect of the present invention that retained potency in relation to glycemic control is associated with reduced mitogenicity, which is a biological consequence of a distinct signaling pathway that is undesirable from the perspective of cancer risk and cancer growth.

It is also envisioned that insulin analogues may be made with A- and B chain sequences derived from animal insulins, such as porcine, bovine, equine, and canine insulins, by way of non-limiting examples, so long as an Aspartic Acid is retained at position B10, Alanine is present at position B12, Glutamic Acid is present at position B29, and one or more acidic amino-acid substututions are optionally present at one or more of the sites provided by A8, A14, A21, and B28. Such variant B chains derived from human insulin or animal insulins may optionally lack Thr$^{B30}$ (des-B30) or contain a C-terminal dipeptide extension (with respective residue positions designated B31 and B32) wherein at least one of these C-terminal extended residues is an acidic amino acid. In addition or in the alternative, the insulin analogue of the present invention may contain a deletion of residues B1, B1-B2, or B1-B3; or may be combined with a variant B chain lacking Proline at position B28 (e.g., Lys$^{B28}$, Ala$^{B28}$ or Gln$^{B28}$ in combination with Glutamic Acid at position B29). At position position A13 may optionally be substituted by Trp or Tyr, position A14 Tyrosine may optionally be substituted by Glutamic Acid, and at position A21 Asparagine may optionally be substituted by Alanine, Glycine or Aspartic Acid.

It is further envisioned that the insulin analogues of the present invention may be derived from Lys-directed proteolysis of a precursor polypeptide in yeast biosynthesis in *Pichia pastoris, Saccharomyces cerevisciae*, or other yeast expression species or strains. Such strains may be engineered to insert penta-fluoro-Phenylalanine at position B24 by means of an engineered tRNA synthetase and orthogonal nonsense suppression. Optionally, the analogues may contain iodo-substitutions within the aromatic ring of Tyr$^{B16}$ and/or Tyr$^{B26}$ (3-mono-iodo-Tyr or [3, 5]-di-iodo-Tyr); intended to augment thermodynamic stability and receptor-binding activity). It is also envisioned that Thr$^{B27}$, Thr$^{B30}$, or one or more Serine residues in the C-domain may be modified, singly or in combination, by a monosaccaride adduct; examples are provided by O-linked N-acetyl-β-D-galactopyranoside (designated GalNAc-O$^{β}$-Ser or GalNAc-O$^{β}$-Thr), O-linked α-D-mannopyranoside (mannose-O$^{β}$-Ser or mannose-O$^{β}$-Thr), and/or α-D-glucopyranoside (glucose-O$^{β}$-Ser or glucose-O$^{β}$-Thr).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Acidic amino acids are Aspartic acid (Asp or D) and Glutamic acid (Glu or E). Introduction of basic amino-acid substitutions (including Lysine (Lys or K), Arginine (Arg or R) and Histidine (His or H)) are not preferred in order to maintain the enhanced net negative charge of this class of analogues. Unless noted otherwise or wherever obvious from the context, the amino acids noted herein should be considered to be L-amino acids. Standard amino acids may also be substituted by non-standard amino acids belonging to the same chemical class.

The amino-acid sequence of human proinsulin is provided, for comparative purposes, as SEQ ID NO: 1.

```
(human proinsulin)
                                        SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn
```

The amino-acid sequence of the A chain of human insulin is provided as SEQ ID NO: 2.

```
(human A chain; residue positions A1-A21)
                                        SEQ ID NO: 2
Gly-Ile-Val-Glu-Gln-Cys-Cys-Thr-Ser-Ile-Cys-Ser- Leu-Tyr-Gln-Leu-Glu-Asn-Tyr-Cys-Asn
```

The amino-acid sequence of the B chain of human insulin is provided as SEQ ID NO: 3.

```
(human B chain; residue positions B1-B30)
                                        SEQ ID NO: 3
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The amino-acid sequence of a modified insulin of the present invention is given in general form in SEQ ID NOS 4 and 5, wherein the six Cysteine residues are paired to provide three disulfide bridges as in wild-type human insulin.

```
A chain
                                        SEQ ID NO: 4
Gly-Ile-Val-Glu-Gln-Cys-Cys-Xaa₁-Ser-Ile-Cys-Ser- Xaa₁₃-Xaa₂-Gln-Leu-Glu-Asn-Tyr-Cys-Xaa₃
```

Where $Xaa_1$ (position A8) may be Thr (as in wild-type insulin), His, Glu or any other non-β-branched amino acid; that is, $Xaa_1$ may be any amino acid other than Val, Leu or Ile. $Xaa_2$ (position A14) may be Tyr (as in wild-type insulin) or Glu. $Xaa_3$ (position A21) may be Asn, Asp, Ala or Gly. It is further envisioned that $Xaa_{13}$ (position A13) may be Leu (as in wild-type human insulin) or be substituted by Trp or Tyr.

```
B chain
                                        SEQ ID NO: 5
Xaa₄-Xaa₅-Xaa₆-Gln-His-Leu-Cys-Gly-Ser-Xaa₁₂-Leu- Val-Glu-Ala-Leu-Tyr-Leu-Val-Cys-Gly-Glu-Arg-Gly- Xaa₇-Phe-Tyr-Thr-Xaa₈-Xaa₉-Thr-Xaa₁₀-Xaa₁₁
```

$Xaa_4$-$Xaa_5$-$Xaa_6$ may be Phe-Val-Asn as in wild-type human insulin or N-terminal deleted variants Val-Asn (des-B1), Asn (des-B1, B2) or omitted (des-B1-B3); where $Xaa_7$ is penta-fluoro-Phenylalanine, a derivative of Phenylalanine in which the five hydrogen atoms in the aromatic ring are simultaneously substituted by fluorine (F); where $Xaa_8$ (position B28) may be Pro (as in wild type), Lys, Ala, Asp, Glu, or Gln; where $Xaa_9$ (position B29) may be Lys (as in wild-type human insulin), Pro (as in insulin lispro), Glu (as in insulin glulisine), Ornithine (Orn; a non-standard amino acid), Ala, or Gln; and where optionally $Xaa_{10}$-$Xaa_{11}$ provides a C-terminal monopeptide or dipeptide extension of the B chain such that at least one amino acid contains an acidic side chain. It is further envisioned that $Xaa_{12}$ (position B10) may be Glu instead of Asp (as in wild-type hman insulin).

The amino-acid sequences of insulin analogues of the present invention are in part given in examples of SEQ ID NOS: 4 and 5, either containing intact B chains or containing N-terminally truncated B chains). For brevity only the specific modifications relative to wild-type human insulin are provided (i.e., specific examples of sequence features $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$, and $Xaa_{11}$). In each of these embodiments residue position B10 is Asp and residue $Xaa_7$ (position B24) is penta-fluoro-Phe ($5F\text{-}Phe^{B24}$):

- $Asp^{B10}$ and $Glu^{B29}$-insulin (in addition to $5F\text{-}Phe^{B24}$);
- $Glu^{A8}$, $Asp^{B10}$, $Glu^{B29}$-insulin (in addition to $5F\text{-}Phe^{B24}$);
- $Glu^{B31}$, $Glu^{B32}$-extended version of $Glu^{A8}$, $Asp^{B10}$, and $Glu^{B29}$-insulin (in addition to $5F\text{-}Phe^{B24}$);
- $Glu^{B31}$, $Glu^{B32}$-extended version of $Asp^{B10}$, $Glu^{B29}$-insulin (in addition to $5F\text{-}Phe^{B24}$);
- $Glu^{B31}$, $Glu^{B32}$-extended version of $Glu^{A8}$, $Asp^{B10}$, $Glu^{B29}$-insulin (in addition to $5F\text{-}Phe^{B24}$;
- $His^{A8}$, $Asp^{B10}$, $Glu^{B29}$-insulin (in addition to $5F\text{-}Phe^{B24}$);
- $Glu^{B31}$, $Glu^{B32}$-extended version of $His^{A8}$, $Asp^{B10}$, and $Glu^{B29}$-insulin (in addition to $5F\text{-}Phe^{B24}$);
- $Glu^{B31}$, $Glu^{B32}$-extended version of $Asp^{B10}$, and $Glu^{B29}$-insulin (in addition to $5F\text{-}Phe^{B24}$);
- $Asp^{B10}$ and $Orn^{B29}$-insulin (in addition to $5F\text{-}Phe^{B24}$);
- $Glu^{A8}$, $Asp^{B10}$, $Orn^{B29}$-insulin (in addition to $5F\text{-}Phe^{B24}$);
- $Glu^{B31}$, $Glu^{B32}$-extended version of $Glu^{A8}$, $Asp^{B10}$, and $Orn^{B29}$-insulin (in addition to $5F\text{-}Phe^{B24}$);
- $Glu^{B31}$, $Glu^{B32}$-extended version of $Asp^{B10}$, $Orn^{B29}$-insulin (in addition to $5F\text{-}Phe^{B24}$);
- $Glu^{B31}$, $Glu^{B32}$-extended version of $Asp^{B10}$, $Orn^{B29}$-insulin (in addition to $5F\text{-}Phe^{B24}$);
- $His^{A8}$, $Asp^{B10}$, $Orn^{B29}$-unsulin (in addition to $5F\text{-}Phe^{B24}$);
- $Glu^{B31}$, $Glu^{B32}$-extended version of $His^{A8}$, $Asp^{B10}$, and $Orn^{B29}$-insulin (in addition to $5F\text{-}Phe^{B24}$);
- $Glu^{B31}$, $Glu^{B32}$-extended version of $Asp^{B10}$, and $Orn^{B29}$-insulin (in addition to $5F\text{-}Phe^{B24}$);
- $Asp^{B10}$, $Lys^{B28}$, and $Pro^{B29}$-insulin (in addition to $5F\text{-}Phe^{B24}$);

Glu$^{48}$, Asp$^{B10}$, Lys$^{B28}$, and Pro$^{B29}$-(in addition to 5F-Phe$^{B24}$);
Glu$^{B31}$, Glu$^{B32}$-extended version of Glu$^{48}$, Asp$^{B10}$, Lys$^{B28}$, and Pro$^{B29}$-insulin (in addition to 5F-Phe$^{B24}$);
Glu$^{B31}$, Glu$^{B32}$-extended version of Asp$^{B10}$, Lys$^{B28}$, and Pro$^{B29}$-insulin (in addition to 5F-Phe$^{B24}$);
Glu$^{B31}$, Glu$^{B32}$-extended version of Glu$^{48}$, Asp$^{B10}$, Lys$^{B28}$, and Pro$^{B29}$-insulin (in addition to 5F-Phe$^{B24}$);
Glu$^{B31}$, Glu$^{B32}$-extended version of Glu$^{48}$, Asp$^{B10}$, Lys$^{B28}$, and Pro$^{B29}$-insulin (in addition 5F-Phe$^{B24}$);
His$^{48}$, Asp$^{B10}$, Lys$^{B28}$, and Pro$^{B29}$-insulin (in addition to 5F-Phe$^{B24}$)
Glu$^{B31}$, Glu$^{B32}$-extended version of His$^{48}$, Asp$^{B10}$, Lyds$^{B28}$, and Pro$^{B29}$-insulin (in addition to 5F-Phe$^{B24}$);
Glu$^{B31}$, Glu$^{B32}$-extended version of Asp$^{B10}$, and Orn$^{B29}$-insulin (in addition to 5F-Phe$^{B24}$);
Asp$^{B10}$ and Asp$^{B28}$-insulin (in addition to 5F-Phe$^{B24}$);
Glu$^{48}$, Asp$^{B10}$, Asp$^{B28}$-insulin (in addition to 5F-Phe$^{B24}$);
Glu$^{B31}$, Glu$^{B32}$-extended version of Glu$_{48}$, and Asp$^{B28}$-insulin (in addition to 5F-Phe$^{B24}$);
Glu$^{B31}$, Glu$^{B32}$-extended version of Asp$^{B10}$, Asp$^{B28}$-insulin (in addition to 5F-Phe$^{B24}$);
Glu$^{B31}$, Glu$^{B32}$-extended version of Glu$^{48}$, Asp$^{B28}$-insulin (in addition to 5F-Phe$^{B24}$);
His$^{48}$, Asp$^{B10}$, Asp$^{B28}$-insulin (in addition to 5F-Phe$^{B24}$);
Glu$^{B31}$, Glu$^{B32}$-extended version of His$^{48}$, Asp$^{B10}$, and Asp$^{B28}$-insulin (in addition to 5F-Phe$^{B24}$);
Glu$^{B31}$, Glu$^{B32}$-extended version of Asp$^{B10}$, and Asp$^{B28}$-insulin (in addition to 5F-Phe$^{B24}$);
Asp$^{B10}$, Asp$^{B28}$, and Orn$^{B29}$-insulin (in addition to 5F-Phe$^{B24}$);
Glu$^{48}$, Asp$^{B10}$, Asp$^{B28}$, and Orn$^{B29}$-insulin (in addition to 5F-Phe$^{B24}$);
Glu$^{B31}$, Glu$^{B32}$-extended version of Glu$^{48}$, Asp$^{B10}$, Asp$^{B28}$, and Orn$^{B29}$-insulin (in addition to 5F-Phe$^{B24}$);
Glu$^{B31}$, Glu$^{B32}$-extended version of Asp$^{B10}$, Asp$^{B28}$, and Orn$^{B29}$-insulin (in addition to 5F-Phe$^{B24}$);
Glu$^{B31}$, Glu$^{B32}$-extended version of Glu$^{48}$, Asp$^{B10}$, Asp$^{B28}$, and Orn$^{B29}$-insulin (in addition to 5F-Phe$^{B24}$);
His$^{48}$, Asp$^{B10}$, Asp$^{B28}$, and Orn$^{B29}$-insulin (in addition to 5F-Phe$^{B24}$);
Glu$^{B31}$, Glu$^{B32}$extended version of His$^{48}$, Asp$^{B10}$, Asp$^{B28}$, and Orn$^{B29}$-insulin (in addition to 5F-Phe$^{B24}$);
Glu$^{B31}$, Glu$^{B32}$-extended version of Asp$^{B10}$, and Asp$^{B28}$-insulin (in addition to 5F-Phe$^{B24}$).

Analogues of the present invention, such as those of SEQ ID NOS 4 and 5, may optionally contain N-terminal deletions of the B chain (des-B1, des-B1-B2 or des-B1-B3) as indicated in the examples below. These N-terminal residues are not required for receptor binding, but their presence in a biosynthetic single-chain precursor is thought to enhance the efficiency of native disulfide pairing in the endoplasmic reticulum and thus production yields. The examples include:

des-(B1-B3) derivative of Asp$^{B10}$ and Glu$^{B29}$-insulin (in addition to 5F-Phe$^{B24}$);
des-(B1-B3) derivative of Glu$^{48}$, Asp$^{B10}$, Glu$^{B29}$-insulin (in addition to 5F-Phe$^{B24}$);
des-(B1-B3) derivative of Glu$^{B31}$, Glu$^{B32}$-extended version of Glu$^{48}$, Asp$^{B10}$, and Glu$^{B29}$-insulin (in addition to 5F-Phe$^{B24}$);
des-(B1-B3) derivative of Glu$^{B31}$, Glu$^{B32}$-extended version of Asp$^{B10}$, Glu$^{B29}$-insulin (in addition to 5F-Phe$^{B24}$);
des-(B1-B3) derivative of Glu$^{B31}$, Glu$^{B32}$-extended version of Glu$^{48}$, Asp$^{B10}$, Glu$^{B29}$-insulin (in addition to 5F-Phe$^{B24}$);
des-(B1-B3) derivative of HiS$^{48}$, Asp$^{B10}$, Glu$^{B29}$-insulin (in addition to 5F-Phe$^{B24}$);
des-(B1-B3) derivative of Glu$^{B31}$, Glu$^{B32}$-extended version of His$^{48}$, Asp$^{B10}$, and Glu$^{B29}$-insulin (in addition to 5F-Phe$^{B24}$);
des-(B1-B3) derivative of Glu$^{B31}$, Glu$^{B32}$-extended version of Asp$^{B10}$, and Glu$^{B29}$-insulin (in addition to 5F-Phe$^{B24}$);
des-(B1-B3) derivative of Asp$^{B10}$ and Orn$^{B29}$-insulin (in addition to 5F-Phe$^{B24}$);
des-(B1-B3) derivative of Glu$^{48}$, Asp$^{B10}$, Orn$^{B29}$-insulin (in addition to 5F-Phe$^{B24}$);
des-(B1-B3) derivative of Glu$^{B31}$, Glu$^{B32}$-extended version of Glu$^{48}$, Asp$^{B10}$, and Orn$^{B29}$-insulin (in addition to 5F-Phe$^{B24}$);
des-(B1-B3) derivative of Glu$^{B31}$, Glu$^{B32}$-extended version of Asp$^{B10}$, Orn$^{B29}$-insulin (in addition to 5F-Phe$^{B24}$);
des-(B1-B3) derivative of Glu$^{B31}$, Glu$^{B32}$-extended version of Glu$^{48}$, Asp$^{B10}$, Orn$^{B29}$-insulin (in addition to 5F-Phe$^{B24}$);
des-(B1-B3) derivative of His$^{48}$, Asp$^{B10}$, Orn$^{B29}$-insulin (in addition to 5F-Phe$^{B24}$);
des-(B1-B3) derivative of Glu$^{B31}$, Glu$^{B32}$-extended version of His$^{48}$, Asp$^{B10}$, and Orn$^{B29}$-insulin (in addition to 5F-Phe$^{B24}$);
des-(B1-B3) derivative of Glu$^{B31}$, Glu$^{B32}$-extended version of Asp$^{B10}$, and Orn$^{B29}$-insulin (in addition to 5F-Phe$^{B24}$);
des-(B1-B3) derivative of Asp$^{B10}$, Lys$^{B28}$, and Pro$^{B29}$-insulin (in addition to 5F-Phe$^{B24}$);
des-(B1-B3) derivative of Glu$^{48}$, Asp$^{B10}$, Lys$^{B28}$, and Pro$^{B29}$-(in addition to 5F-Phe$^{B24}$);
des-(B1-B3) derivative of Glu$^{B31}$, Glu$^{B32}$-extended version of Glu$^{48}$, Asp$^{B10}$, Lys$^{B28}$, and Pro$^{B29}$-insulin (in addition to 5F-Phe$^{B24}$);
des-(B1-B3) derivative of Glu$^{B31}$, Glu$^{B32}$-extended version of Asp$^{B10}$, Lys$^{B28}$, and Pro$^{B29}$-insulin (in addition to 5F-Phe$^{B24}$);
des-(B1-B3) derivative of Glu$^{B31}$, Glu$^{B32}$-extended version of Glu$^{48}$, Asp$^{B10}$, Lys$^{B28}$, and Pro$^{B29}$-insulin (in addition to 5F-Phe$^{B24}$);
des-(B1-B3) derivative of His$^{48}$, Asp$^{B10}$, Lys$^{B28}$, and Pro$^{B29}$-insulin (in addition to 5F-Phe$^{B24}$);
des-(B1-B3) derivative of Glu$^{B31}$, Glu$^{B32}$-extended version of His$^{48}$, Asp$^{B10}$, Lys$^{B28}$, and Pro$^{B29}$-insulin (in addition to 5F-Phe$^{B24}$);
Glu$^{B31}$, Glu$^{B32}$-extended version os Asp$^{B10}$, and Orn$^{B29}$-insulin (in addition to 5F-Phe$^{B24}$);
des-(B1-B3) derivative of Asp$^{B10}$ and Asp$^{B28}$-insulin (in addition to 5F-Phe$^{B24}$);
des-(B1-B3) derivative of Glu$^{48}$,Asp$^{B10}$-insulin (in addition to 5F-Phe$^{B24}$);
Glu$^{B31}$, Glu$^{B32}$-extended version of Glu$^{48}$, Asp$^{B10}$, and Asp$^{B28}$-insulin (in addition to 5F-Phe$^{B24}$);
des-(B1-B3) derivative of Glu$^{B31}$, Glu$^{B32}$-extended version of Asp$^{B10}$, Asp$^{B28}$-insulin (In addition to 5F-Phe$^{B24}$);
des-(B1-B3) derivative of Glu$^{B31}$, Glu$^{B32}$-extended version of Glu$^{48}$, Asp$^{B10}$, Asp$^{B28}$-insulin (in addition to 5F-Phe$^{B24}$);
des-(B1-B3) derivative of His$^{48}$, Asp$^{B10}$, Asp$^{B28}$-insulin (in addition to 5F-Phe$^{B24}$);
des-(B1-B3) derivative of Glu$^{B31}$, Glu$^{B32}$-extended version of His$^{48}$, Asp$^{B10}$, Asp$^{B28}$-insulin (in addition to 5F-Phe$^{B24}$);

des-(B1-B3) derivative of Glu$^{B31}$, Glu$^{B32}$-extended version of Asp$^{B10}$, and Asp$^{B28}$-insulin (in addition to 5F-Phe$^{B24}$);

des-(B1-B3) derivative of Asp$^{B10}$, Asp$^{B28}$, and Orn$^{B29}$-insulin (in addition to 5F-Phe$^{B24}$);

des-(B1-B3) derivative of Glu$^{48}$, Asp$^{B10}$, Asp$^{B28}$, and Orn$^{B29}$-insulin (in addition to 5F-Phe$^{B24}$);

des-(B1-B3) derivative of Glu$^{B31}$, Glu$^{B32}$-extended version of Glu$^{48}$, Asp$^{B10}$, Asp$^{B28}$, and Ornhu$^{B29}$-insulin (in addition to 5F-Phe$^{B24}$);

des-(B1-B3) derivative of Glu$^{B31}$, Glu$^{B32}$-extended version of Asp$^{B10}$, Asp$^{B28}$; and Orn$^{B29}$-insulin (in addition to 5F-Phe$^{B24}$);

des-(B1-B3) derivative of Glu$^{B31}$, Glu$^{B32}$-extended version of Glu$^{48}$, Asp$^{B10}$, Asp$^{B28}$, and Orn$^{B29}$-insulin (in addition to 5F-Phe$^{B24}$);

des-(B1-B3) derivative of His$^{48}$, Asp$^{B10}$, Asp$^{B28}$, and Orn$^{B29}$-m$^{B29}$-insulin (in addition to 5F-Phe$^{B24}$);

des-(B1-B3) derivative of Glu$^{B31}$, Glu$^{B32}$-extended version of His$^{48}$, Asp$^{B10}$, Asp$^{B28}$, and Orn$^{B29}$-insulin (in addition to 5F-Phe$^{B24}$);

des-(B1-B3) derivative of Glu$^{B31}$, Glu$^{B32}$-extended version of Asp$^{B10}$, and Asp$^{B28}$-insulin (in addition to 5F-Phe$^{B24}$).

The following DNA sequences encode single-chain insulin analogues with codons optimized for usage patterns in *Pichia pastoris*. These single-chain insulin analogues provide biosynthetic intermediates for the production of the above two-chain insulin analogues. In each case the final codon (AAT) represents a stop codon.

The sense strand of a gene encoding a 53-residue single-chain insulin analogue with substitutions AspB10 and GluB30 and with C-domain Trp-Lys is given in SEQ ID NO: 6.

SEQ ID NO: 6
TTCGTCAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTACTTCCATCTGCTCATTGTACCAATTGGAGAAC

TACTGCAACTAA

The sense strand of a gene encoding a 53-residue single-chain insulin analogue with substitutions AspB10 and AlaB30 and with C-domain Ala-Lys is given in SEQ ID NO: 7.

SEQ ID NO: 7
TTCGTCAATCAACACTTGTGTGGTAGTGACTTGGTCGAGGCTTTGTACTT

GGTCTGTGGTGAGAGAGGATTCTTCTACACCCCTAAGGCTGCTAAGGGAA

TCGTTGAGCAATGCTGTACTTCCATCTGCTCATTGTACCAATTGGAGAAC

TACTGCAACTAA

The sense strand of a gene encoding a 53-residue single-chain insulin analogue with substitutions AspB10, GluA8 and GluB30 and with C-domain Trp-Lys is given in SEQ ID NO: 8.

SEQ ID NO: 8
TTCGTCAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTGAATCCATCTGCTCATTGTACCAATTGGAGAAC

TACTGCAACTAA

The sense strand of a gene encoding a 53-residue single-chain insulin analogue with substitution AspB10 and GluB30 and with C-domain Trp-Lys such that a non-standard amino acid may be inserted through nonsense suppression at codon position B24 (TAG) is given in SEQ NO: 9.

SEQ ID NO: 9
TTCGTCAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTACTTCCATCTGCTCATTGTACCAATTGGAGAAC

TACTGCAACTAA

The sense strand of a gene encoding a 53-residue single-chain insulin analogue with substitution GluA8, AspB10 and GluB30 and with C-domain Trp-Lys such that a non-standard amino acid may be inserted through nonsense suppression at codon position B24 (TAG) is given in SEQ ID NO: 10.

SEQ ID NO: 10
TTCGTCAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTGAATCCATCTGCTCATTGTACCAATTGGAGAAC

TACTGCAACTAA

The group of synthetic genes provided in SEQ ID NOS: 11-15 provides a set of DNA sequences that optionally encode optional amino-acid substitutions at positions A13 and A14 in accordance with the amino-acid sequences specified above. It is known in the art that in the nuclear genes of yeasts, Leucine is encoded by DNA codons TTA, TTG, CTT, CTC, and CTG; that Tyrosine is encoded by DNA codons TAT and TAC; that Tryptophan is encoded by DNA codon TGG; and that Glutamic acid is encoded by DNA codons GAA and GAG.

SEQ ID NO: 11 provides the sense strand of a gene encoding a 53-residue single-chain insulin analogue with substitutions AspB10 and GluB30, with C-domain Trp-Lys such that the codon at position A13 (XXX$_1$) encodes Leucine, Tyrosine or Trptophan and such that the codon at position A14 (XXX$_2$) encodes Tyrosine or Glutamic Acid.

SEQ ID NO: 11
TTCGTCAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTACTTCCATCTGCTCA-XXX$_1$-XXX$_2$-CAATTGG

AGAACTACTGCAACTAA

XXX$_1$ is TTA, TTG, CTT, CTC, CTG, TAT, TAC or TGG

XXX$_2$ is TAT, TAC, GAA or GAG

SEQ ID NO: 12 provides the sense strand of a gene encoding a 53-residue single-chain insulin analogue with substitutions AspB10 and AlaB30 and with C-domain Ala-Lys such that the codon at position A13 (XXX$_1$) encodes Leucine, Tyrosine or Trptophan and the codon at position A14 (XXX$_2$) encodes Tyrosine or Glutamic Acid.

SEQ ID NO: 12
TTCGTCAATCAACACTTGTGTGGTAGTGACTTGGTCGAGGCTTTGTACTT

GGTCTGTGGTGAGAGAGGATTCTTCTACACCCCTAAGGCTGCTAAGGGAA

TCGTTGAGCAATGCTGTACTTCCATCTGCTCA-XXX$_1$-XXX$_2$-CAATTGG

AGAACTACTGCAACTAA

XXX$_1$ is TTA, TTG, CTT, CTC, CTG, TAT, TAC or TGG

XXX$_2$ is TAT, TAC, GAA or GAG

SEQ ID NO: 13 provides the sense strand of a gene encoding a 53-residue single-chain insulin analogue with substitutions AspB10, GluA8 and GluB30 and with C-domain Trp-Lys such that the codon at position A13 (XXX$_1$) encodes Leucine, Tyrosine or Trptophan and such that the codon at position A14 (XXX$_2$) encodes Tyrosine or Glutamic Acid.

SEQ ID NO: 13
TTCGTCAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTGAATCCATCTGCTCA-XXX$_1$-XXX$_2$-CAATTGG

AGAACTACTGCAACTAA

XXX$_1$ is TTA, TTG, CTT, CTC, CTG, TAT, TAC or TGG

XXX$_2$ is TAT, TAC, GAA or GAG

SEQ ID NO: 14 provides the sense strand of a gene encoding a 53-residue single-chain insulin analogue with substitution AspB10 and GluB30 and with C-domain Trp-Lys such that a non-standard amino acid may be inserted through nonsense suppression at codon position B24 (TAG), such that the codon at position A13 (XXX$_1$) encodes Leucine, Tyrosine or Tryptophan and such that the codon at position A14 (XXX$_2$) encodes Tyrosine or Glutamic Acid.

SEQ ID NO: 14
TTCGTCAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTACTTCCATCTGCTCA-XXX$_1$-XXX$_2$-CAATTGG

AGAACTACTGCAACTAA

XXX$_1$ is TTA, TTG, CTT, CTC, CTG, TAT, TAC or TGG

XXX$_2$ is TAT, TAC, GAA or GAG

SEQ ID NO: 15 provides the sense strand of a gene encoding a 53-residue single-chain insulin analogue with substitution GluA8, AspB10 and GluB30 and with C-domain Trp-Lys such that a non-standard amino acid may be inserted through nonsense suppression at codon position B24 (TAG), such that the codon at position A13 (XXX$_1$) encodes Leucine, Tyrosine or Trptophan and such the codon at position A14 (XXX$_2$) encodes Tyrosine or Glutamic Acid.

SEQ ID NO: 15
TTCGTCAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTGAATCCATCTGCTCA-XXX$_1$-XXX$_2$-CAATTGG

AGAACTACTGCAACTAA

XXX$_1$ is TTA, TTG, CTT, CTC, CTG, TAT, TAC or TGG

XXX$_2$ is TAT, TAC, GAA or GAG

The following group of synthetic sequneces, SEQ ID NOS: 16-30 provided below, provides a set of DNA sequences that, in addition to the sequence features defined in SEQ ID NOS: 11-15, optionally encode a Lysine residue at one of the following three codon positions: B1, B2 or B3; such Lysine substitutions in a biosynthetic single-chain insulin precursor would enable production of insulin analogues of the present invention whose B chains contain N-terminal deletions des-B1, des-B1, B2, or des-B1-B3 in accordance with the amino-acid sequences specified above. These N-terminal truncations are respectively directed by substitution of Lysine at positions B1, B2 or B3 in the biosynthetic single-chain insulin precursor. It is known in the art that in nuclear genes of yeasts, Lysine is encoded by DNA codons AAA and AAG (or AAR). As indicated above, it is also known in the art that in the nuclear genes of yeasts, Leucine is encoded by DNA codons TTA, TTG, CTT, CTC, and CTG; that Tyrosine is encoded by DNA codons TAT and TAC; that Tryptophan is encoded by DNA codon TGG; and that Glutamic acid is encoded by DNA codons GAA and GAG (GAR).

SEQ ID NO: 16 provides the sense strand of a gene encoding a 53-residue single-chain insulin analogue with substitutions AspB10 and GluB30, with C-domain Trp-Lys such that the codon at position A13 (XXX$_1$) encodes Leucine, Tyrosine or Trptophan, such that the codon at position A14 (XXX$_2$) encodes Tyrosine or Glutamic Acid, and such that the first codon of the B-chain sequence (AAR) encodes Lysine.

SEQ ID NO: 16
AARGTCAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTACTTCCATCTGCTCA-XXX$_1$-XXX$_2$-CAATTGG

AGAACTACTGCAACTAA

XXX$_1$ is TTA, TTG, CTT, CTC, CTG, TAT, TAC or TGG

XXX$_2$ is TAT, TAC, GAA or GAG

SEQ ID NO: 17 provides the sense strand of a gene encoding a 53-residue single-chain insulin analogue with substitutions AspB10 and AlaB30 and with C-domain Ala-Lys such that the codon at position A13 (XXX$_1$) encodes Leucine, Tyrosine or Trptophan, such that the codon at position A14 (XXX$_2$) encodes Tyrosine or Glutamic Acid, and such that the first codon of the B-chain sequence encodes Lysine.

SEQ ID NO: 17
AARGTCAATCAACACTTGTGTGGTAGTGACTTGGTCGAGGCTTTGTACTT

GGTCTGTGGTGAGAGAGGATTCTTCTACACCCCTAAGGCTGCTAAGGGAA

TCGTTGAGCAATGCTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

SEQ ID NO: 18 provides the sense strand of a gene encoding a 53-residue single-chain insulin analogue with substitutions AspB10, GluA8 and GluB30 and with C-domain Trp-Lys such that the codon at position A13 (XXX₁) encodes Leucine, Tyrosine or Trptophan, such that the codon at position A14 (XXX₂) encodes Tyrosine or Glutamic Acid, and such that the first codon of the B-chain sequence encodes Lysine.

SEQ ID NO: 18
AARGTCAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTGAATCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitution AspB10 and GluB30 and with C-domain Trp-Lys such that a non-standard amino acid may be inserted through nonsense suppression at codon position B24 (TAG), such that the codon at position A13 (XXX₁) encodes Leucine, Tyrosine or Trptophan, such that the codon at position A14 (XXX₂) encodes Tyrosine or Glutamic Acid, and such that the first codon of the B-chain sequence encodes Lysine.

SEQ ID NO: 19
AARGTCAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitution GluA8, AspB10 and GluB30 and with C-domain Trp-Lys such that a non-standard amino acid may be inserted through nonsense suppression at codon position B24 (TAG), such that the codon at position A13 (XXX₁) encodes Leucine, Tyrosine or Trptophan, such the codon at position A14 (XXX₂) encodes Tyrosine or Glutamic Acid, and such that the first codon of the B-chain sequence encodes Lysine.

SEQ ID NO: 20
AARGTCAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTGAATCCATCTGCTCA-XXX₁-XXX₂-CAATTGG

AGAACTACTGCAACTAA

XXX₁ is TTA, TTG, CTT, CTC, CTG, TAT, TAC or TGG.

XXX₂ is TAT, TAC, GAA or GAG.

The following sequence provides the sense strand of a gene encoding a 53-residue single-chain insulin analogue with substitutions AspB10 and GluB30, with C-domain Trp-Lys such that the codon at position A13 (XXX₁) encodes Leucine, Tyrosine or Trptophan, such that the codon at position A14 (XXX₂) encodes Tyrosine or Glutamic Acid, and such that the second codon of the B-chain sequence encodes Lysine.

SEQ ID NO: 21
TTCAARAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitutions AspB10 and AlaB30 and with C-domain Ala-Lys such that the codon at position A13 (XXX₁) encodes Leucine, Tyrosine or Trptophan, such that the codon at position A14 (XXX₂) encodes Tyrosine or Glutamic Acid, and such that the second codon of the B-chain sequence encodes Lysine.

SEQ ID NO: 22
TTCAARAATCAACACTTGTGTGGTAGTGACTTGGTCGAGGCTTTGTACTT

GGTCTGTGGTGAGAGAGGATTCTTCTACACCCCTAAGGCTGCTAAGGGAA

TCGTTGAGCAATGCTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitutions AspB10, GluA8 and GluB30 and with C-domain Trp-Lys such that the codon at position A13 (XXX₁) encodes Leucine, Tyrosine or Trptophan, such that the codon at position A14 (XXX₂) encodes Tyrosine or Glutamic Acid, and such that the second codon of the B-chain sequence encodes Lysine.

SEQ ID NO: 23
TTCAARAATCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTGAATCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitution AspB10 and GluB30 and with C-domain Trp-Lys such that a non-standard amino acid may be inserted through nonsense suppression at codon position B24 (TAG), such that the codon at position A13 (XXX₁) encodes Leucine, Tyrosine or Trptophan, such that the codon at position A14 (XXX₂) encodes Tyrosine or Glutamic Acid, and such that the second codon of the B-chain sequence encodes Lysine.

SEQ ID NO: 24
TTCAARAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT. TAC, GAA or GAG

The following sequence provides the sense strand of a gene encoding a 53-residue single-chain insulin analogue with substitution GluA8, AspB10 and GluB30 and with C-domain Trp-Lys such that a non-standard amino acid may be inserted through nonsense suppression at codon position B24 (TAG), such that the codon at position A13 (XXX₁) encodes Leucine, Tyrosine or Trptophan, such the codon at position A14 (XXX₂) encodes Tyrosine or Glutamic Acid, and such that the second codon of the B-chain sequence encodes Lysine.

SEQ ID NO: 25
TTCAARAATCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTGAATCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitutions AspB10 and GluB30, with C-domain Trp-Lys such that the codon at position A13 (XXX₁) encodes Leucine, Tyrosine or Trptophan, such that the codon at position A14 (XXX₂) encodes Tyrosine or Glutamic Acid, and such that the third codon of the B-chain sequence encodes Lysine.

SEQ ID NO: 26
TTCGTCAARCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitutions AspB10 and AlaB30 and with C-domain Ala-Lys such that the codon at position A13 (XXX₁) encodes Leucine, Tyrosine or Trptophan, such that the codon at position A14 (XXX₂) encodes Tyrosine or Glutamic Acid, and such that the third codon of the B-chain sequence encodes Lysine.

SEQ ID NO: 27
TTCGTCAARCAACACTTGTGTGGTAGTGACTTGGTCGAGGCTTTGTACTT

GGTCTGTGGTGAGAGAGGATTCTTCTACACCCCTAAGGCTGCTAAGGGAA

TCGTTGAGCAATGCTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitutions AspB10, GluA8 and GluB30 and with C-domain Trp-Lys such that the codon at position A13 (XXX₁) encodes Leucine, Tyrosine or Trptophan, such that the codon at position A14 (XXX₂) encodes Tyrosine or Glutamic Acid, and such that the third codon of the B-chain sequence encodes Lysine.

SEQ ID NO: 28
TTCGTCAARCAACACTTGTGTGGTAGTGACTTGGTCGAGGCATTGTACTT

GGTCTGTGGTGAGAGAGGATTCTTCTACACCCCAAAGGAGTGGAAGGGTA

TCGTTGAGCAATGTTGTGAATCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG

The following sequence provides the sense strand of a gene encoding a 53-residue single-chain insulin analogue with substitution AspB10 and GluB30 and with C-domain Trp-Lys such that a non-standard amino acid may be inserted through nonsense suppression at codon position B24 (TAG), such that the codon at position A13 (XXX₁) encodes Leucine, Tyrosine or Trptophan, such that the codon at position A14 (XXX₂) encodes Tyrosine or Glutamic Acid, and such that the third codon of the B-chain sequence encodes Lysine.

SEQ ID NO: 29
TTCGTCAARCAACACTTGTGTGGTAGTGACTTGGTCGAGGCATTGTACTT

GGTCTGTGGTGAGAGAGGATAGTTCTACACCCCAAAGGAGTGGAAGGGTA

-continued

```
TCGTTGAGCAATGTTGTACTTCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG
```

The following sequence provides the sense strand of a gene encoding a 53-residue single-chain insulin analogue with substitution GluA8, AspB10 and GluB30 and with C-domain Trp-Lys such that a non-standard amino acid may be inserted through nonsense suppression at codon position B24 (TAG), such that the codon at position A13 (XXX₁) encodes Leucine, Tyrosine or Trptophan, such the codon at position A14 (XXX₂) encodes Tyrosine or Glutamic Acid, and such that the third codon of the B-chain sequence encodes Lysine.

```
                                          SEQ ID NO: 30
TTCGTCAARCAACACTTGTGTGGTAGTGACTTGGTCGAGGCATTGTACTT

GGTCTGTGGTGAGAGAGGATAGTTCTACACCCCAAAGGAGTGGAAGGGTA

TCGTTGAGCAATGTTGTGAATCCATCTGCTCA-XXX₁-XXX₂-CAATTGG

AGAACTACTGCAACTAA

XXX₁ is TTA, TTG, CTT, CTC, CTG, TAT, TAC or TGG

XXX₂ is TAT, TAC, GAA or GAG
```

Two single-chain insulin analogues of the present invention were prepared by biosynthesis of a precursor polypeptide in *Pichia pastoris*; this system secretes a folded protein containing native disulfide bridges with cleavage N-terminal extension peptide. Tryptic cleavage of this precursor protein yields a two-chain insulin fragment containing a truncated B chain beginning at residue PheB1 and ending at ArgB22 and a complete A chain. The precursor polypeptides are encoded by synthetic genes whose sequences are within the general description of SEQ ID NOS: 4 and 5, which in each case contain the substitution AspB10 and may optionally contain the additional substitutions GluA8, TrpA13, TyrA13, and/or GluA14. Single-chain insulin precursors are also envisaged containing a nonsense codon at position B24 such that non-standard amino-acid substitutions may be inserted via an engineered orthogonal tRNA synthetase; such precursors would not be processed by trypsin but instead split by a lysine-specific endopeptidase.

We envision two related sets of DNA sequences may encode manufacturing intermediates such that either (i) Glutamic Acid at position B29 is introduced into an insulin analogue via semi-synthesis employing a synthetic C-terminal B-chain peptide containing Glutamic acid at final position B29 or (ii) Glutamic Acid at position B29 may be introduced directly into the single-chain biosynthetic precursor via the standard genetic code.

We further envision two related sets of DNA sequences may encode manufacturing intermediates such that either (i) penta-fluoro-Phe at position B24 is introduced into an insulin analogue via semi-synthesis employing a synthetic C-terminal B-chain peptide containing penta-fluoro-Phe at final position B24 or (ii) penta-fluoro-Phe at position B24 may be introduced directly into the single-chain biosynthetic precursor via the extended genetic-code technology employing a nonsense codon at position B24 and an orthogonal engineered tRNA synthetase.

Two single-chain insulin analogues of the present invention were prepared by trypsin-mediated semi-synthesis following biosynthesis of a precursor polypeptide in *Pichia pastoris*; this system secretes a folded protein containing native disulfide bridges with cleavage N-terminal extension peptide. One embodiment contains the substitutions $Asp^{B10}$, $Lys^{B28}$, and $Pro^{B29}$ in addition to penta-fluoro-Phe at position B24 (Sigselin-1); the second embodiment contains the substitutions $Asp^{B10}$ and $Orn^{B29}$ in addition to penta-fluoro-Phe at position B24. Tryptic cleavage of this precursor protein yields a two-chain insulin fragment containing a truncated B chain beginning at residue $Phe^{B1}$ and ending at $Arg^{B22}$ (amino acids 1-22 of SEQ ID NO: 5) and a complete A chain (SEQ ID NO:4). The precursor polypeptide for Segeselin-1 may be enoded by a polynucleotide generalized as SEQ ID NO: 31.

(Asp B10, 5F-Phe B24, Lispro)

```
                                          SEQ ID NO: 31
TTCGTCAATCAACACTTGTGTGGTAGTGACTTGGTCGAGGCATTGTACTT

GGTCTGTGGTGAGAGAGGATAGTTCTACACCAARCCNACNXXXAARGGNA

TCGTTGAGCAATGTTGTACTTCCATCTGCTCATTGTACCAATTGGAGAAC

TACTGCAACTAA

XXX is TGG or GCN
```

Single-chain insulin precursors are also envisaged containing a nonsense codon at position B24 such that non-standard amino-acid substitutions may be inserted via an engineered orthogonal tRNA synthetase; such precursors would not be processed by trypsin but instead split by a lysine-specific endopeptidase.

Native-like structure is retained. The far-UV CD spectrum of Sigselin-1 closely resembles that of KP-insulin or the $Asp^{B10}$-derivative of KP-insulin. The thermodynamic stabilities of Sigselin-1 were probed by CD-monitored guanidine denaturation. The method was as described (Hua, Q. X., et al. *J. Biol. Chem.* 283, 14703-16 (2008)). The results indicate that this analogue is more stable to chemical denaturation than is either wild-type insulin, KP-insulin, or $Asp^{B10}$ derivative of KP-insulin (as probed at 25° C. and pH 7.4 by CD-detected guanidine denaturation). Free energies of unfolding ($\Delta G_u$) were as follows: WT insulin, 3.3 kcal/mole; insulin lispro, 2.8 kcal/mole; and Sigselin-1, 4.8 kcal/mole. Given the challenges posed to formulation of Humalog® by the instability of KP-insulin ($\Delta\Delta G_u 0.5(\pm 0.2)$ kcal/mole relative to WT), the augmented stability of Sigselin-1 ($\Delta\Delta G_u 1.5(\pm 0.2)$ kcal/mole) predicts a stable formulation.

Assay for MCF-7Colony Formation in Soft Agar. The $Asp^{B10}$ substitution is known in the art to enhance the affinity of insulin for the IR by twofold, block zinc-mediated hexamer assembly, and favorably augment the hormone's intrinsic stability. Indeed, the clinical development of $Asp^{B10}$-insulin as a pioneering candidate rapid-acting insulin was halted by Novo Nordisk due to the unexpected observation of excess mammary tumors in Sprague-Dawley rats following one year of treatment. A considerable literature ensued describing the mitogenic activity of $Asp^{B10}$-insulin in cell-culture studies of human neoplastic cell lines. To addresss this concern given the presence of $Asp^{B10}$ in analogues of the present invention (or $Glu^{B10}$ in an alternative set of embodiments), an assay of mitogenicity was performed as follows.

Figure 6:
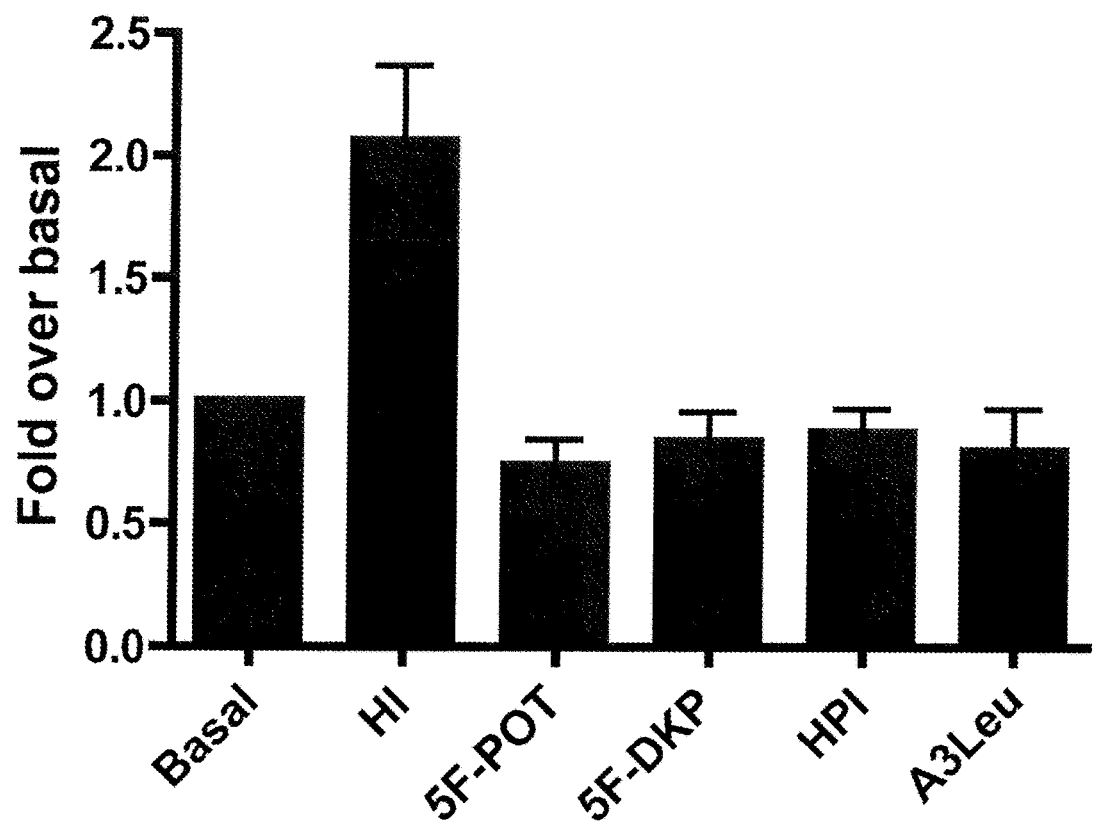
FIG. 6 provides an assay measuring the mitogenicity of insulin analogues: histogram showing MCF-7 cell colony formation in soft agar. Data indicate the relative number of colonies>100 nm in diameter under each condition compared to basal. Abbreviations: HI, wild-type human insulin; 5F-POT is 5F-Phe$^{B24}$-Orn$^{B29}$-insulin; 5F-DKP is 5F-Phe$^{B24}$-Asp$^{B10}$-KP-insulin insulin (Sigselin-1); HPI, wild-type human proinsulin; A3Leu, inactive insulin analogue containing substitution Val$^{A3}$→Leu ("insulin Wakayama").

This background motivated comparative studies of insulin analogs' ability to stimulate the proliferation of human breast-cancer cell line MCF-7. MCF-7 cells is known in the art to express three homologous receptors (IR-A, IR-B and IGF-1R) and so provide a model for an insulin-responsive malignancy with relative mitogenicities IGF-I >$Asp^{B10}$-insulin>wild-type insulin. In our preliminary assays MCF-7 cells ($1.5 \times 10^3$ cells in 0.75 ml, obtained from ATCC cat #HTB-22), were mixed with an equal volume Bacto-agar at 42° C. This 0.3% agar suspension was poured over a 1.5-ml base of 0.6% agar in 12-well plates and overlaid with basal growth medium with (or without) insulin or insulin analogues at a protein concentration of 100 nM, which was replenished 3× per week. Plates were incubated at 37° C. in a $CO_2$ tissue-culture incubator for 3 weeks, at which time colonies were stained with crystal violet and counted under an inverted microscope. A positive control was provided by IGF-I (not shown) and a negative control by medium lacking insulin or an insulin analogue ("basal" in FIG. 6). Whereas WT insulin at high doses enhances MCF-7 cell proliferation in accordance with published studies, our results indicate that Sigselin-1 (labeled "5F-DKP" in FIG. 6) exhibits negligible mitogenicity, indistinguishable from that of a related penta-fluoro-$Phe^{B24}$ analogue lacking $Asp^{B10}$ ("5F-POT") and in accordance with the negligible activities of human proinsulin ("HPI") and inactive analogue $Leu^{A3}$-insulin.

Figure 7:
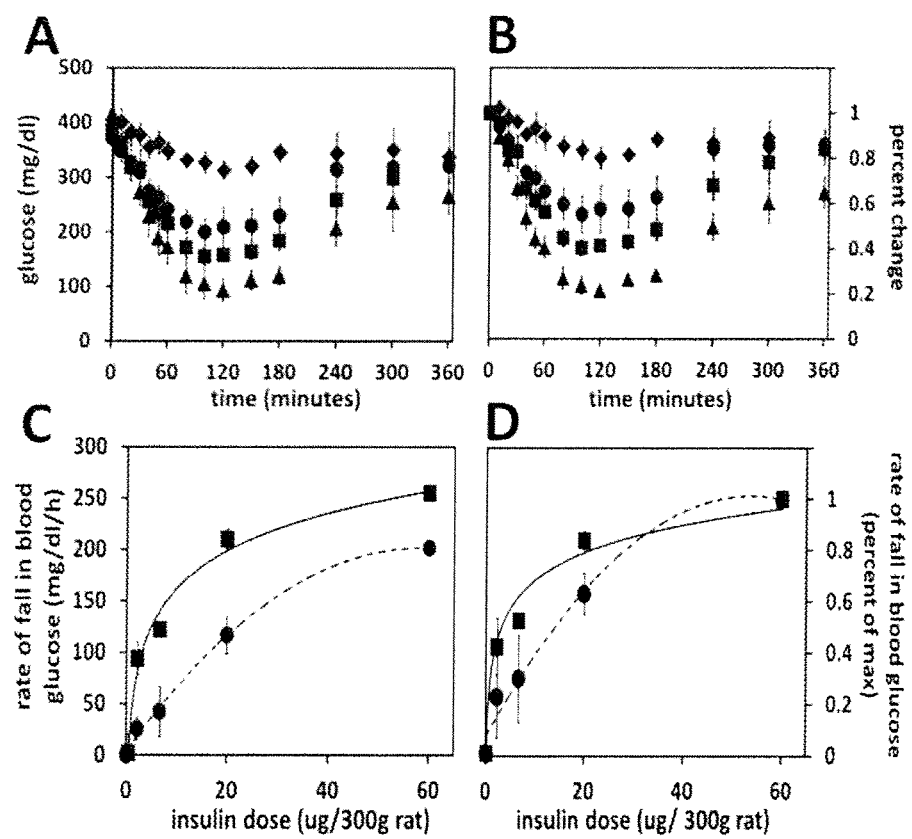
FIG. 7 provides an assay measuring the glucose-lower activity in STZ Lewis rats. (A and B) Time course of average BG following 11.5 nmoles/kg SQ injection in 6 rats at time=0: (squares) KP-insulin, (diamonds) Asp$^{B10}$-KP-insulin, (circles) 5F-phe$^{B24}$-KP-insulin, and (triangles) 5F-Phe$^{B24}$-Asp$^{B10}$-insulin (Sigselin-1). (C and D) Dose-response curves for Sigselin-1 (circles) and KP-insulin (squares) in relation to fall in BG concentration observed in the first 60 min following SQ injection.

Biological activity and pharmacodynamics were tested in male Lewis rats (ca. 300 g) rendered diabetic by streptozotocin (FIG. 7). PD effects of s.q. injection of four representative insulin analogues, each containing the core three substitutions ($Asp^{B10}$, $Ala^{B12}$ and $Glu^{B29}$ in the presence or absence of other optional design elements), were evaluated in relation to Humalog® and an $Asp^{B10}$ derivative of insulin lispro (DKP-insulin); the resulting overall profile of the blood-glucose concentration indicated that the PD properties of Sigselin-1 is similar to that of Humalog® but at a protein dose (defined in nanomoles) defined such that 1 unit of Sigselin-1 requires three times as many protein molecules as 1 unit of KP-insulin. In these assays the rats were injected subcutaneously (SQ); blood was obtained at successive intervals from clipped tail tip. Average blood-glucose (BG) concentration and percent change from the initial BG respectively were plotted (FIGS. 7A and 7B). Studies were repeated for 4 different doses of Sigselin-1 and lispro (absolute and percent changes in FIGS. 7C and 7D) to determine potency (defined as fall in BG in first 60 min following SQ injection) per mg (which varies among marketed insulin products).

These data show that whereas the penta-fluoro-$Phe^{B24}$ (5F-$Phe^{B24}$) derivative of insulin lispro exhibits negligible biological activity (diamonds in FIGS. 7A and 7B), biological activity is rescued by co-modification $His^{B10} \rightarrow Asp$ (circles) relative to insulin lispro (KP-insulin; squares). $Asp^{B10}$ also augments the activity of KP-insulin but in less dramatic fashion (diamonds). Dose-response studies of 5F-$Phe^{B24}$-$Asp^{B10}$-KP-insulin (Sigselin-1) relative to KP-insulin demonstrated that threefold nanomoles of the Sigselin were required to achieve equivalent therapeutic effects, as is true for current insulin product insulin detemir (Levemir®; Novo-Nordisk).

Together, the above cell-based and rat-based findings provide evidence that Sigselin-1 can direct signaling events that lead to a therapeutic hypoglycemic response without stimulating mitogenic pathways in an insulin-responsive and IGF-I-responsive human cancer cell line.

Evidence of selective signaling in non-diabetic Sprague-Dawley rats. The pharmacodynamics (PD) of Sigselin-1 was investigated in hyperinsulinemic-euglycemic clamp (HIEC) studies of non-diabetic rats in which endogenous β-cell insulin secretion was suppressed by octreotide (a somatostatin analog). Four rats were employed per group. These baseline studies verified that a threefold dose of Sigselin-1 infusion (in moles/min/kg) conferred a therapeutic strength equivalent to insulin lispro.

Figure 8:
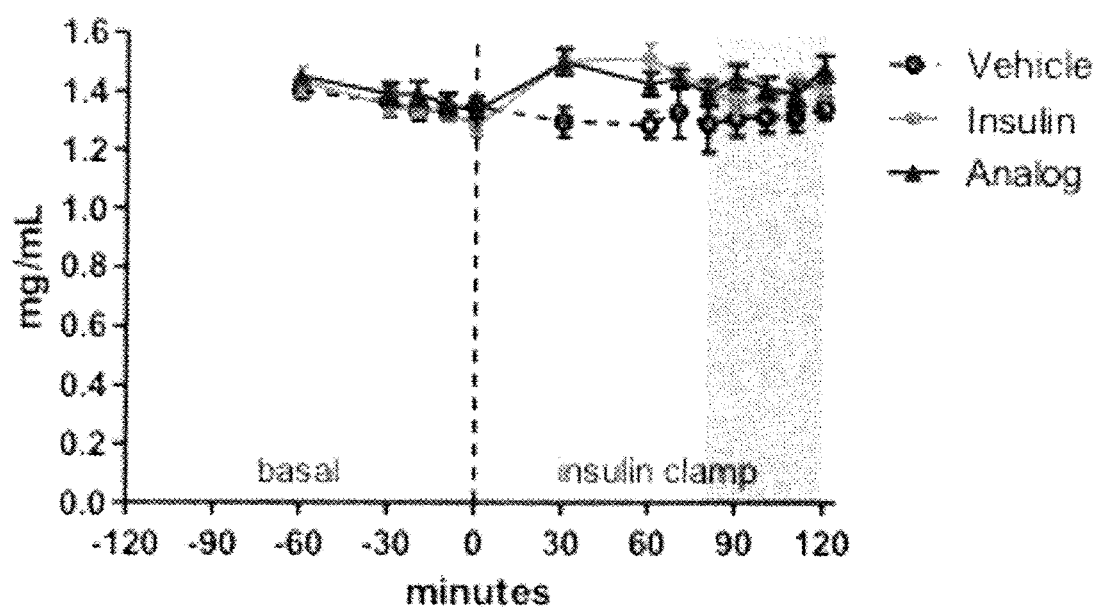
FIG. 8 provides data pertaining to hyperinsulinemic-euglycemic clamp (HIEC) studies. Time course of blood-glucose (BG) concentration given in units of mg/ml (instead of usual mg/dl). Data validate clamp technique (N=4 rats per arm).

Evidence of selective signaling was sought using a titriated-glucose tracer technique. In brief, after 30 min of acclimatization to the HIEC environment, a prime-continuous infusion (bolus 20.8 μCi, then 0.52 μCi/min) of [$^3$H-3]-glucose (Perkin-Elmer NEN) was started and maintained throughout the study as described. After 30 min of tracer equilibration, blood samples for glucose and plasma radioactivity were taken at every 10-min for 30 min to establish a baseline. BG was measured real-time during the HIEC using a GM7 Micro-stat Analyzer (ANALOX Instruments). At time-zero, a prime-continuous infusion of insulin lispro (1.5 mU/kg/min) or Sigselin-1 (threefold in mg/ml protein) and a variable infusion of 25% ordinary glucose solution (IVX Animal Health) were started. The rate of glucose infusion was adjusted as needed to clamp the plasma glucose concentration at 130-140 mg/dl. Blood samples were taken every 10 min during the 60-min hyperinsulinemic period. Plasma radioactivity from [$^3$H-3]-glucose was determined after deproteinization with $Ba(OH)_2$ and $ZnSO_4$ and evaporation to remove tritiated water. Plasma insulin levels were measured at 60, 90, 120, 150, and 180 min. In an analogous protocol, we employed [$^{14}$C]-2-deoxyglucose (20 μCi of [$^{14}$C]2-deoxy-glucose in 100 μL saline) as a probe to measure tissue-specific relative rates of insulin-stimulated glucose uptake during the final 40 min of the clamp (gray zone in FIG. 8).

Figure 9:
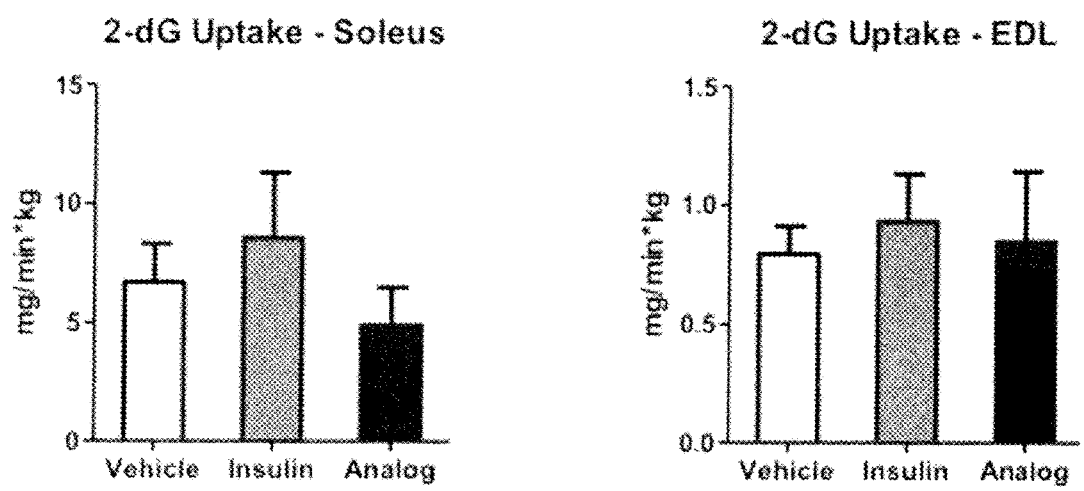
FIG. 9 provides an assay of muscle update of $^{14}$C-tracer 2-deoxyglucose: vehicle control, "insulin" (insulin lispro), and "analog" (Sigselin-1).

To evaluate post-receptor signaling bias, we focused on two muscles, the slow-twitch Soleus and the fast-twitch extensor digitorum longus (EDL). Rates of insulin-directed glucose uptake in these muscles, as probed with [$^{14}$C]-2-deoxyglucose, were similar between insulin lispro and Sigselin-1, and similar to vehicle; this result was expected given the low doses of insulins used in these studies (FIG. 9).

Figure 10:
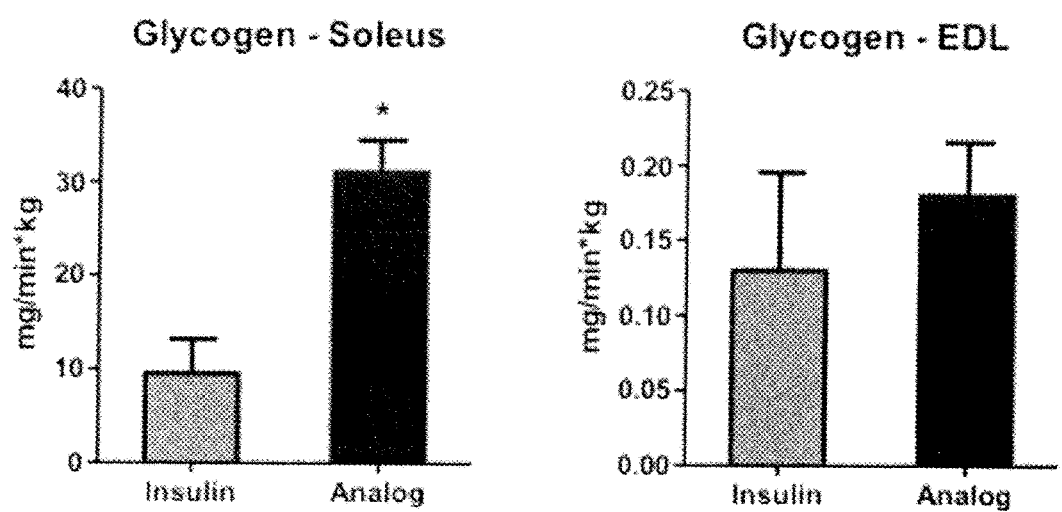
FIG. 10 provides an assay muscle-specific incorporation of $^{3}$H-labeled glucose into glycogen: "insulin" (insulin lispro), and "analog" (Sigselin-1).

Nonetheless, relative rates of incorporation of [$^3$H-3]-glucose into glycogen were much higher in the Soleus following signaling by Sigselin-1 than following signaling by lispro (FIG. 10, left) despite equal rates of glucose uptake in Soleus of WT insulin-treated compared to Sigselin-l-treated animals; a similar trend was seen in the EDL but did not achieve statistical significance (N=4 rats). These findings are remarkable and suggest that the flow of glucose-derived $^3$H-C is preferentially going to glycogen (relative to oxidation or lipid synthesis). Less fat in muscle could reduce insulin resistance, which would be of great clinical significance.

A method for treating a patient with diabetes mellitus comprises administering a two-chain insulin analogue as described herein. It is another aspect of the present invention that the two-chain insulin analogues may be prepared either in yeast (*Pichia pastoris*) or subject to total chemical synthesis by native fragment ligation. The synthetic route of preparation is preferred in the case of non-standard modifications, such as D-amino-acid substitutions or O-linked modifications of Serine or Threonine by carbohydrates; however, it would be feasible to manufacture a subset of the single-chain analogues containing non-standard modifications by means of extended genetic-code technology or four-base codon technology (for review, see Hohsaka, T., & Sisido, M., 2012). It is yet another aspect of the present invention that use of non-standard amino-acid substitutions can augment the resistance of the two-chain insulin analogue to chemical degradation or to physical degradation. We further envision the analogues of the present invention providing a method for the treatment of diabetes mellitus or the metabolic syndrome. The route of delivery of the insulin analogue is by subcutaneous injection through the use of a syringe or pen device. An insulin analogue of the present invention may also contain other modifications, such as substitutions at positions A13 and/or A14. An insulin analogue of the present invention may also contain a foreshortened B-chain due to deletion of residues B1-B3 or a C-terminal-extended B chain containing an acidic residue at position B31 or at least one acidic residue in a two-residue extension B31-B32.

A pharmaceutical composition may comprise such insulin analogues and which may optionally include zinc. Because the insulin analogues of the present invention do not form classical zinc-stabilized hexamers (and indeed do not require such assembly for stability), zinc ions may be included at varying zinc ion:protein ratios lower than are typically employed in formulations containing a predominance of insulin hexamers; such ratios may be in the range 0.01-0.10 moles of zinc ions per mole of insulin analogue. The pH of the formulation is in the range pH 7.0-8.0; a buffer (typically sodium phosphate or Tris-hydrochloride) may or may not be present. In such a formulation, the concentration of the insulin analogue would typically be between about 0.6-5.0 mM; concentrations up to 5 mM may be used in vial or pen; the more concentrated formulations (U-200 or higher) may be of particular benefit in patients with marked insulin resistance. Excipients may include glycerol, glycine, arginine, Tris, other buffers and salts, and anti-microbial preservatives such as phenol and meta-cresol; the latter preservatives are known to enhance the stability of the insulin hexamer. Non-ionic surfactants such as Tween-20 may also be added to augment physical stability. Such a pharmaceutical composition may be used to treat a patient having diabetes mellitus or other medical condition by administering a physiologically effective amount of the composition to the patient.

Based upon the foregoing disclosure, it should now be apparent that the two-chain insulin analogues provided will carry out the objects set forth hereinabove. Namely, these insulin analogues exhibit biological activity (as defined by the nanomoles of protein monomer required to lower the blood-glucose concentration in a mammal on subcutaneous or intravenous injection) similar to that of wild-type insulin such that rapid action is retained with reduced mitogenicity. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Barnes-Seeman, D., Beck, J., and Springer, C. (2014) Fluorinated compounds in medicinal chemistry: recent applications, synthetic advances and matched-pair analyses. Curr. Top. Med. Chem. 14:855-64.

Brange J, editor. (1987) Galenics of Insulin: The Physicochemical and Pharmaceutical Aspects of Insulin and Insulin Preparations. Berlin: Springer Berlin Heidelberg.

Hohsaka, T., and Sisido, M. (2012) Incorporation of non-natural amino acids into proteins. Curr. Opin. Chem. Biol. 6, 809-15.

Liu, M., Hua, Q. X., Hu, S. Q., Jia, W., Yang, Y., Saith, S. E., Whittaker, J., Aryan, P., and Weiss, M. A. (2010) Deciphering the hidden informational content of protein sequences: foldability of proinsulin hinges on a flexible arm that is dispensable in the mature hormone. J. Biol. Chem. 285:30989-1001.

Vølund, A., Brange, J., Drejer, K., Jensen, I., Markussen, J., Ribel, U., Sorensen, A. R., and Schlichtkrull, J. (1991) In vitro and in vivo potency of insulin analogues designed for clinical use. Diabet. Med. 8:839-47.

Wang, Z. X. (1995) An exact mathematical expression for describing competitive biding of two different ligands to a protein molecule FEBS Lett. 360: 111-114.

Whittaker, J., and Whittaker, L. (2005) Characterization of the functional insulin binding epitopes of the full-length insulin receptor. J. Biol. Chem. 280: 20932-20936.

Yang, Y., Petkova, A., Huang, K., Xu, B., Hua, Q. X., Ye, I. J., Chu, Y. C., Hu, S. Q., Phillips, N. B., Whittaker, J., Ismail-Beigi, F., Mackin, R. B., Katsoyannis, P. G., Tycko, R., and Weiss, M. A. (2010) An Achilles' heel in an amyloidogenic protein and its repair: insulin fibrillation and therapeutic design. J. Biol. Chem. 285:10806-21.

Yuvienco, C., More, H, T., Haghpanah, J. S., Tu, R. S., and Montclare, J. K. (2012) Modulating supramolecular assemblies and mechanical properties of engineered protein materials by fluorinated amino acids. Biomacromolecules 13:2273-8.

---

What is claimed is:

1. A method of lowering the blood sugar level of a patient, the method comprising administering to the patient in need thereof a pharmaceutical formulation comprising an insulin analogue containing a B-chain polypeptide having an Asp substitution at position B10 relative to wild type human insulin and a penta-fluoro-Phe substitution at position B24 relative to wild type human insulin.

2. The method according to claim 1, wherein the B-chain polypeptide additionally comprises a Glu substitution at position B29 relative to wild type human insulin.

3. The method according to claim 1, wherein the B-chain polypeptide additionally comprises a substitution at position B28 relative to human insulin, selected from the group consisting of Lys, Gln, and Ala.

4. The method according to claim 3, wherein the substitution at position B28 relative to human insulin is Lys, and additionally comprising a Pro substitution at position B29 relative to human insulin.

5. The method according to claim 1, wherein the B-chain polypeptide additionally comprises an N-terminal deletion of the B-chain polypeptide of one to three amino acids.

6. The method according to claim 1, wherein the pharmaceutical formulation additionally comprises an A-chain polypeptide containing one or more of the substitutions, relative to wild type human insulin, selected from the group consisting of:
   a substitution at position A8 selected from any amino acid other than Val, Leu and Ile;
   a substitution at position A13 selected from Trp or Tyr;
   a Tyr substitution at position A14; and
   a substitution at position A21 selected from the group consisting of Asn, Asp, Ala and Gly.

7. The method according to claim 1, wherein the formulation contains zinc ions at a molar ratio of between 0.00 and 0.10 zinc ions per insulin analogue monomer and wherein the pH of the formulation is between pH 7.0 and pH 8.0.

8. The method according to claim 7, where the insulin analogue formulation is formulated at a strength of at least U-100.

9. The method according to claim 8, where the insulin analogue formulation is formulated at a strength of at least U-500.

10. The method according to claim 9, where the insulin analogue formulation is formulated at a strength of between U-500 and U-1000.

11. The method according to claim 5, additionally comprising an A-chain polypeptide containing one or more of the substitutions, relative to wild type human insulin, selected from the group consisting of:
    a substitution at position A8 selected from any amino acid other than Val, Leu and Ile;
    a substitution at position A13 selected from Trp or Tyr;
    a Tyr substitution at position A14; and
    a substitution at position A21 selected from the group consisting of Asn, Asp, Ala and Gly.

12. The method according to claim 11, wherein the formulation contains zinc ions at a molar ratio of between 0.00 and 0.10 zinc ions per insulin analogue monomer and wherein the pH of the formulation is between pH 7.0 and pH 8.0.

* * * * *

SEQUENCE LISTING

```
<160> NUMBER OF SEQ ID NOS: 31

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
```

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
                20                  25                  30

<210> SEQ ID NO 4
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is any amino acid other than Val, Leu or
      Ile
<220> FEATURE:
<221> NAME/KEY: MISC_FEATURE
<222> LOCATION: (13)..(13)
<223> OTHER INFORMATION: Xaa is Leu, Trp or Tyr
<220> FEATURE:
<221> NAME/KEY: MISC_FEATURE
<222> LOCATION: (14)..(14)
<223> OTHER INFORMATION: Xaa is Tyr or Glu
<220> FEATURE:
<221> NAME/KEY: MISC_FEATURE
<222> LOCATION: (21)..(21)
<223> OTHER INFORMATION: Xaa is Asn, Asp, Ala or Gly

<400> SEQUENCE: 4

Gly Ile Val Glu Gln Cys Cys Xaa Ser Ile Cys Ser Xaa Xaa Gln Leu
1               5                   10                  15

Glu Asn Tyr Cys Xaa
            20

<210> SEQ ID NO 5
<211> LENGTH: 32
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Xaa is Phe-Val-Asn, Val-Asn, Asn or no amino
      acids
<220> FEATURE:
<221> NAME/KEY: MISC_FEATURE -continued

```
<222> LOCATION: (10)..(10)
<223> OTHER INFORMATION: Xaa is Glu or Asp
<220> FEATURE:
<221> NAME/KEY: MISC_FEATURE
<222> LOCATION: (24)..(24)
<223> OTHER INFORMATION: Xaa is penta-fluoro-Phenylalanine
<220> FEATURE:
<221> NAME/KEY: MISC_FEATURE
<222> LOCATION: (28)..(28)
<223> OTHER INFORMATION: Xaa is Pro, Lys, Ala, Asp, Glu or Gln
<220> FEATURE:
<221> NAME/KEY: MISC_FEATURE
<222> LOCATION: (29)..(29)
<223> OTHER INFORMATION: Xaa is Lys, Pro, Glu, Ornithine, Ala, or Gln
<220> FEATURE:
<221> NAME/KEY: MISC_FEATURE
<222> LOCATION: (31)..(32)
<223> OTHER INFORMATION: Xaa is no amino acid or at least one amino acid
      is Glu or Asp

<400> SEQUENCE: 5

Xaa Xaa Xaa Gln His Leu Cys Gly Ser Xaa Leu Val Glu Ala Leu Tyr
 1               5                  10                  15

Leu Val Cys Gly Glu Arg Gly Xaa Phe Tyr Thr Xaa Xaa Thr Xaa Xaa
             20                  25                  30

<210> SEQ ID NO 6
<211> LENGTH: 162
<212> TYPE: DNA
<213> ORGANISM: Homo sapiens

<400> SEQUENCE: 6
ttcgtcaatc aacacttgtg tggtagtgac ttggtcgagg cattgtactt ggtctgtggt     60
gagagaggat tcttctacac cccaaaggag tggaagggta tcgttgagca atgttgtact    120
tccatctgct cattgtacca attggagaac tactgcaact aa                      162

<210> SEQ ID NO 7
<211> LENGTH: 162
<212> TYPE: DNA
<213> ORGANISM: Homo sapiens

<400> SEQUENCE: 7
ttcgtcaatc aacacttgtg tggtagtgac ttggtcgagg ctttgtactt ggtctgtggt     60
gagagaggat tcttctacac ccctaaggct gctaagggaa tcgttgagca atgctgtact    120
tccatctgct cattgtacca attggagaac tactgcaact aa                      162

<210> SEQ ID NO 8
<211> LENGTH: 162
<212> TYPE: DNA
<213> ORGANISM: Homo sapiens

<400> SEQUENCE: 8
ttcgtcaatc aacacttgtg tggtagtgac ttggtcgagg cattgtactt ggtctgtggt     60
gagagaggat tcttctacac cccaaaggag tggaagggta tcgttgagca atgttgtgaa    120
tccatctgct cattgtacca attggagaac tactgcaact aa                      162

<210> SEQ ID NO 9
<211> LENGTH: 162
<212> TYPE: DNA
<213> ORGANISM: Homo sapiens

<400> SEQUENCE: 9
ttcgtcaatc aacacttgtg tggtagtgac ttggtcgagg cattgtactt ggtctgtggt     60
```

```
gagagaggat agttctacac cccaaaggag tggaagggta tcgttgagca atgttgtact      120
tccatctgct cattgtacca attggagaac tactgcaact aa                        162
```

<210> SEQ ID NO 10
<211> LENGTH: 162
<212> TYPE: DNA
<213> ORGANISM: Homo sapiens

<400> SEQUENCE: 10

```
ttcgtcaatc aacacttgtg tggtagtgac ttggtcgagg cattgtactt ggtctgtggt       60
gagagaggat agttctacac cccaaaggag tggaagggta tcgttgagca atgttgtaa      120 tccatctgct cattgtacca attggagaac tactgcaact aa                         162
```

<210> SEQ ID NO 11
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 11

```
ttcgtcaatc aacacttgtg tggtagtgac ttggtcgagg cattgtactt ggtctgtggt       60
gagagaggat tcttctacac cccaaaggag tggaagggta tcgttgagca atgttgtact      120
tccatctgct cannnnnnca attggagaac tactgcaact aa                         162
```

<210> SEQ ID NO 12
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 12

```
ttcgtcaatc aacacttgtg tggtagtgac ttggtcgagg ctttgtactt ggtctgtggt       60
gagagaggat tcttctacac ccctaaggct gctaagggaa tcgttgagca atgctgtact      120
tccatctgct cannnnnnca attggagaac tactgcaact aa                         162
```

<210> SEQ ID NO 13
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 13
ttcgtcaatc aacacttgtg tggtagtgac ttggtcgagg cattgtactt ggtctgtggt    60
gagagaggat tcttctacac cccaaaggag tggaagggta tcgttgagca atgttgtgaa   120
tccatctgct cannnnnnca attggagaac tactgcaact aa                      162

<210> SEQ ID NO 14
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 14
ttcgtcaatc aacacttgtg tggtagtgac ttggtcgagg cattgtactt ggtctgtggt    60
gagagaggat agttctacac cccaaaggag tggaagggta tcgttgagca atgttgtact   120
tccatctgct cannnnnnca attggagaac tactgcaact aa                      162

<210> SEQ ID NO 15
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 15
ttcgtcaatc aacacttgtg tggtagtgac ttggtcgagg cattgtactt ggtctgtggt    60
gagagaggat agttctacac cccaaaggag tggaagggta tcgttgagca atgttgtgaa   120
tccatctgct cannnnnnca attggagaac tactgcaact aa                      162

<210> SEQ ID NO 16
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 16
aargtcaatc aacacttgtg tggtagtgac ttggtcgagg cattgtactt ggtctgtggt    60
gagagaggat tcttctacac cccaaaggag tggaagggta tcgttgagca atgttgtact   120
tccatctgct cannnnnnca attggagaac tactgcaact aa                      162

<210> SEQ ID NO 17
<211> LENGTH: 162
<212> TYPE: DNA
<213> ORGANISM: Homo sapiens
<220> FEATURE:
<221> NAME/KEY: misc_feature

```
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 17
aargtcaatc aacacttgtg tggtagtgac ttggtcgagg ctttgtactt ggtctgtggt      60
gagagaggat tcttctacac ccctaaggct gctaagggaa tcgttgagca atgctgtact     120
tccatctgct cannnnnnca attggagaac tactgcaact aa                        162

<210> SEQ ID NO 18
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 18
aargtcaatc aacacttgtg tggtagtgac ttggtcgagg cattgtactt ggtctgtggt      60
gagagaggat tcttctacac cccaaaggag tggaagggta tcgttgagca atgttgtgaa     120
tccatctgct cannnnnnca attggagaac tactgcaact aa                        162

<210> SEQ ID NO 19
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 19
aargtcaatc aacacttgtg tggtagtgac ttggtcgagg cattgtactt ggtctgtggt      60
gagagaggat agttctacac cccaaaggag tggaagggta tcgttgagca atgttgtact     120
tccatctgct cannnnnnca attggagaac tactgcaact aa                        162

<210> SEQ ID NO 20
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 20
aargtcaatc aacacttgtg tggtagtgac ttggtcgagg cattgtactt ggtctgtggt      60
gagagaggat agttctacac cccaaaggag tggaagggta tcgttgagca atgttgtgaa     120
```
tccatctgct cannnnnnca attggagaac tactgcaact aa                              162

<210> SEQ ID NO 21
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 21
ttcaaraatc aacacttgtg tggtagtgac ttggtcgagg cattgtactt ggtctgtggt           60
gagagaggat tcttctacac cccaaaggag tggaagggta tcgttgagca atgttgtact          120
tccatctgct cannnnnnca attggagaac tactgcaact aa                             162

<210> SEQ ID NO 22
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 22
ttcaaraatc aacacttgtg tggtagtgac ttggtcgagg ctttgtactt ggtctgtggt           60
gagagaggat tcttctacac ccctaaggct gctaagggaa tcgttgagca atgctgtact          120
tccatctgct cannnnnnca attggagaac tactgcaact aa                             162

<210> SEQ ID NO 23
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 23
ttcaaraatc aacacttgtg tggtagtgac ttggtcgagg cattgtactt ggtctgtggt           60
gagagaggat tcttctacac cccaaaggag tggaagggta tcgttgagca atgttgtgaa          120
tccatctgct cannnnnnca attggagaac tactgcaact aa                             162

<210> SEQ ID NO 24
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 24
ttcaaraatc aacacttgtg tggtagtgac ttggtcgagg cattgtactt ggtctgtggt    60
gagagaggat agttctacac cccaaaggag tggaagggta tcgttgagca atgttgtact   120
tccatctgct cannnnnnca attggagaac tactgcaact aa                      162

<210> SEQ ID NO 25
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 25
ttcaaraatc aacacttgtg tggtagtgac ttggtcgagg cattgtactt ggtctgtggt    60
gagagaggat agttctacac cccaaaggag tggaagggta tcgttgagca atgttgtgaa   120
tccatctgct cannnnnnca attggagaac tactgcaact aa                      162

<210> SEQ ID NO 26
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 26
ttcgtcaarc aacacttgtg tggtagtgac ttggtcgagg cattgtactt ggtctgtggt    60
gagagaggat agttctacac cccaaaggag tggaagggta tcgttgagca atgttgtact   120
tccatctgct cannnnnnca attggagaac tactgcaact aa                      162

<210> SEQ ID NO 27
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 27
ttcgtcaarc aacacttgtg tggtagtgac ttggtcgagg ctttgtactt ggtctgtggt    60
gagagaggat tcttctacac ccctaaggct gctaagggaa tcgttgagca atgctgtact   120
tccatctgct cannnnnnca attggagaac tactgcaact aa                      162

<210> SEQ ID NO 28

```
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 28
ttcgtcaarc aacacttgtg tggtagtgac ttggtcgagg cattgtactt ggtctgtggt      60
gagagaggat tcttctacac cccaaaggag tggaagggta tcgttgagca atgttgtgaa     120
tccatctgct cannnnnnca attggagaac tactgcaact aa                        162

<210> SEQ ID NO 29
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 29
ttcgtcaarc aacacttgtg tggtagtgac ttggtcgagg cattgtactt ggtctgtggt      60
gagagaggat agttctacac cccaaaggag tggaagggta tcgttgagca atgttgtact     120
tccatctgct cannnnnnca attggagaac tactgcaact aa                        162

<210> SEQ ID NO 30
<211> LENGTH: 162
<212> TYPE: DNA
<213> ORGANISM: Homo sapiens
<220> FEATURE:
<221> NAME/KEY: misc_feature
<222> LOCATION: (133)..(135)
<223> OTHER INFORMATION: NNN is TTA, TTG, CTT, CTC, CTG, TAT, TAC or TGG
<220> FEATURE:
<221> NAME/KEY: misc_feature
<222> LOCATION: (136)..(138)
<223> OTHER INFORMATION: NNN is TAT, TAC, GAA or GAG

<400> SEQUENCE: 30
ttcgtcaarc aacacttgtg tggtagtgac ttggtcgagg cattgtactt ggtctgtggt      60
gagagaggat agttctacac cccaaaggag tggaagggta tcgttgagca atgttgtgaa     120
tccatctgct cannnnnnca attggagaac tactgcaact aa                        162

<210> SEQ ID NO 31
<211> LENGTH: 162
<212> TYPE: DNA
<213> ORGANISM: Homo sapiens
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
```

```
<222> LOCATION: (91)..(93)
<223> OTHER INFORMATION: NNN is TGG or GCN
<220> FEATURE:
<221> NAME/KEY: misc_feature
<222> LOCATION: (99)..(99)
<223> OTHER INFORMATION: n is a, c, g, or t

<400> SEQUENCE: 31
ttcgtcaatc aacacttgtg tggtagtgac ttggtcgagg cattgtactt ggtctgtggt      60
gagagaggat agttctacac caarccnacn nnnaarggna tcgttgagca atgttgtact     120
tccatctgct cattgtacca attggagaac tactgcaact aa                       162
```